US006429315B1

(12) United States Patent
Sledeski et al.

(10) Patent No.: US 6,429,315 B1
(45) Date of Patent: Aug. 6, 2002

(54) PROCESS FOR PREPARING N6-SUBSTITUTED ADENOSINE DERIVATIVES

(75) Inventors: Adam W. Sledeski, Collegeville, PA (US); Luc Grondard, Courcouronnes (FR); Matthew R. Powers, Barto, PA (US); Tory H. Powner, Chester, VA (US); Michael K. O'Brien, Berwyn; Ching T. Tsuei, Lansdale, both of PA (US); Patrick Leon, Tassin la Demi Lune (FR); Gregory G. Kubiak, Wilmington, DE (US); Laurence Pailleres-Hubert, Maisons-Alfort; Benoit Viguier, Orleans, both of (FR)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/489,276

(22) Filed: Jan. 21, 2000

Related U.S. Application Data

(63) Continuation of application No. PCT/US99/29841, filed on Dec. 15, 1999.
(60) Provisional application No. 60/114,486, filed on Dec. 31, 1998, now abandoned, and provisional application No. 60/116,028, filed on Jan. 15, 1999.

(51) Int. Cl.⁷ .............................................. C07D 471/02
(52) U.S. Cl. .................... 546/118; 544/264; 536/27.11; 536/27.2; 536/27.23
(58) Field of Search .......................... 536/27.11, 27.2, 536/27.23; 544/264; 546/118

(56) References Cited

U.S. PATENT DOCUMENTS

| 5,364,862 A | 11/1994 | Spada et al. |
| 5,561,134 A | 10/1996 | Spada et al. |
| 5,631,383 A | 5/1997 | Largeau et al. |
| 5,652,366 A | 7/1997 | Spada et al. ................. 546/118 |
| 5,670,679 A | 9/1997 | Baker et al. |
| 5,684,159 A | 11/1997 | O'Brien et al. |
| 5,736,554 A | 4/1998 | Spada et al. ................. 514/303 |
| 5,808,093 A | 9/1998 | O'Brien et al. |
| 6,143,894 A | 11/2000 | O'Brien et al. ............. 546/118 |
| 6,235,909 B1 | 5/2001 | Garcia et al. ................ 546/296 |

FOREIGN PATENT DOCUMENTS

| WO | W O 92/05177 A1 | 4/1992 |
| WO | W O 97/24327 A1 | 7/1997 |
| WO | WO 98/01426 | 1/1998 |
| WO | W O 98/11064 A1 | 3/1998 |
| WO | WO98/11064 A1 | 3/1998 |
| WO | WO98/25921 A1 | 6/1998 |
| WO | W O 98/25921 A1 | 6/1998 |
| WO | WO00/40584 A2 | 7/2000 |
| WO | W O 00/40584 A2 | 7/2000 |

*Primary Examiner*—Gary Geist
*Assistant Examiner*—L Eric Crane
(74) *Attorney, Agent, or Firm*—Paul R. Darkes; Irving Newman; William C. Coppola

(57) ABSTRACT

This invention is directed to a process for preparing N6-substituted adenosine derivatives, to intermediates useful therefor and to methods of preparing these intermediates.

18 Claims, No Drawings

PROCESS FOR PREPARING N6-SUBSTITUTED ADENOSINE DERIVATIVES

CROSS REFERENCE TO RELATED APPLICATIONS

This is a continuation of International Patent Application No. PCT/US99/29841, filed Dec. 15, 1999, which is, in turn, a continuation of U.S. patent application Ser. No. 60/114,486, filed Dec. 31, 1998, now abandoned, and U.S. patent application Ser. No. 60/116,028, filed Jan. 15, 1999.

TECHNICAL FIELD

This invention is directed to a process for preparing N6-substituted adenosine derivatives, to intermediates useful therefor and to methods of preparing these intermediates.

BACKGROUND OF THE INVENTION

N6-substituted adenosine derivatives, as exempliified by [1S-[1a,2b,3b,4a(S*)]]-4-[7-[[1-(3-chloro-2-thienyl)methyl]propyl]amino]-3 H-imidazo[4,5-b]pyridin-3-yl]-N-ethyl-2,3-dihydroxycyclopentanecarboxamide, are useful as a cardiovascular agents, more particularly as antihypertenisive and anti-ischemic agents, as cardioprotective agents which ameliorate ischemic injury or myocardial infarct size consequent to myocardial ischemia, and as antilipolytic agents which reduce plasma lipid levels, serum triglyceride levels, and plasma cholesterol levels. See U.S. Pat. Nos. 5,364,862 and 5,561,134 and International Patent Application No. PCT/US97/11320.

Methods of preparing these compounds and intermediates thereto are disclosed in U.S. Pat. Nos. 5,364,862 and 5,561,134 and Internationial Patent Application Nos. PCT/US97/11320, PCT/US97/15729 and PCT/US97/21439.

SUMMARY OF THE INVENTION

This invention is directed to a process for preparing an N-protected N6-substituted adenosine compound of formula

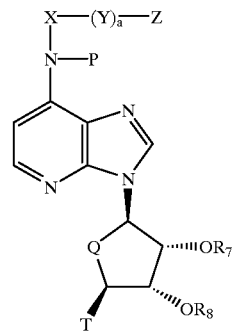

wherein
P is a nitrogenl protecting group;
Q is $CH_2$ or O;
T is

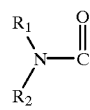

or $R_3O-CH_2$;

X is a straight or branched chain alkylene, cycloakylyene or cycloalkenylene group;
Y is $NR_4$, O or S;
a=0 or 1;
Z is of the formula

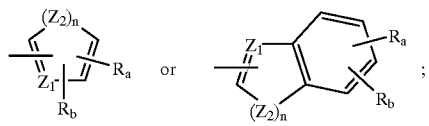

$Z_1$ is N, $CR_5$, $(CH)_m-CR_5$ or $(CH)_m-N$, m being 1 or 2;
$Z_2$ is N, $NR_6$, O or S;
n is 0 or 1;
$R_1$, $R_2$, $R_3$, $R_4$, $R_5$ and $R_6$ are independently H, alkyl, aryl or heterocyclyl;
$R_7$ and $R_8$ are independently H, alkyl, aralkyl, carbamoyl, alkyl carbamoyl, dialkylcarbamoyl, acyl, alkoxycarbonyl, aralkoxycarbonyl, or aryloxycarbonyl; or $R_7$ and $R_8$ together may form

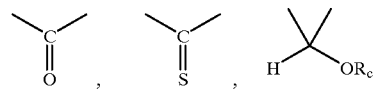

where $R_c$ is hydrogen or alkyl,

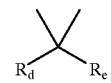

where $R_d$ and $R_e$ are independently hydrogen, or alkyl, or $R_d$ and $R_e$ together with the carbon atom to which they are attached may form a 1,1-cycloalkyl group; and
$R_a$ and $R_b$ are independently H, OH, alkyl, hydroxyalkyl, alkyl mercaptyl, thioalkyl, alkoxy, alkyoxyalkyl, amino, alkyl amino, carboxyl, acyl, halogen, carbamoyl, alkyl carbamoyl, aryl or heterocyclyl, this process comprising reacting a 4-N-protected-2,3,4-triaminopyridine compound of formula

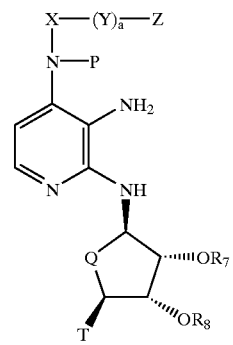

with a formic acid derivative.

The process of the present invention offers improved yields, purity, ease of preparation and/or isolation of intermediates and final product, and more industrially useful reaction conditions and workability over previously disclosed methods of preparation.

DETAILED DESCRIPTION OF THE INVENTION

Definitions of Terms

As used above and throughout the description of the invention, the following terms, unless otherwise indicated, have the following meanings:

"Acyl" means a straight or branched alkyl-C=O group. "Thioacyl" means a straight or branched alkyl-C=S group. Preferred acyl and thioacyl groups are lower alkanoyl and lower thioalkanloyl having from 1 to about 6 carbon atoms in the alkyl group.

"Alkyl" means a saturated aliphatic hydrocarbon group which may be straight or branched and has 1 to about 20 carbon atoms in the chain. Preferred alky groups may be straight or branched and has 1 to about 10 carbon atoms in the chain. Branched means that a lower alkyl group such as methyl, ethyl or propyl is attached to a linear alkyl chain.

"Lower alkyl" means an alkyl group having 1 to about 6 carbons.

"Cycloalkyl" means an aliphatic ring having 3 to about 10 carbon atoms in the ring. Preferred cycloalkyl groups have 4 to about 7 carbon atoms in the ring.

"Carbamoyl" means an

group. Alkylcarbamoyl and dialkylcarbamoyl means that the nitrogen of the carbamoyl is substituted by one or two alkyl groups, respectively.

"Carboxyl" means a COOH group.

"Alkoxy" means an alkyl-O, group in which "alkyl" is as previously described. Lower alkoxy groups are preferred. Exemplary groups include methoxy, ethoxy, n-propoxy, i-propoxy and n-butoxy.

"Alkoxyalkyl" means an alkyl group, as previously described, substituted by an alkoxy group, as previously described.

"Alkoxycarbonyl means an alkoxy-C=O group.

"Aralkyl" means an alkyl group substituted by an aryl radical, wherein "aryl" means a phenyl or naphthyl. "Substituted aralkyl" and "substituted aryl" means that the aryl group, or the aryl group of the aralkyl group is substituted with one or more substituents which include alkyl, alkoxy, amino, nitro, carboxy, carboalkoxy, cyano, alkyl amino, halo, hydroxy, hydroxyalkyl, mercaptyl, alkylmercaptyl, trihaloalkyl, carboxyalkyl or carbamoyl.

"Aralkoxycarbonyl" means an aralkyl-O-C=O group.

"Aryloxycarbonyl" means an aryl-O-C=O group.

"Carbalkoxy" means a carboxyl substituent esterified with an alcohol of the formula $C_nH_{2n+1}OH$, wherein n is from 1 to about 6.

"Halogen" (or "halo") means chlorine (chloro), fluorine (fluoro), bromine (bromo) or iodine (iodo).

"Heterocyclyl" means about a 4 to about a 10 membered ring structure in which one or more of the atoms in the ring is an element other than carbon, e.g., N, O or S. Heterocyclyl may be aromatic or non-aromatic, i.e., may be saturated, partially or fully unsaturated. Preferred heterocyclyl groups include pyridyl, pyridazinyl, pyrimidinyl, isoquinolinyl, quinoliniyl, quinazolinyl. imidazolyl, pyrrolyl, furanyl, thienyl, thiazolyl, benzothiazolyl, piperidinyl, pyrrolidinyl, tetrahydrofuranyl, tetrahydropyranyl, and morphonlinyl groups.

"Substituted heterocyclyl" means that the heterocyclyl group is substituted by one or more substituents wherein the substituents include alkoxy, alkylainino, aryl, carbalkoxy, carbamoyl, cyano, halo, heterocyclyl, trihalomethyl, hydroxy, mercaptyl, alkylmercaptyl or nitro.

"Hydroxyalkyl" means an alkyl group substituted by a hydroxy group. Hydroxy lower alkyl groups are preferred. Exemplary preferred groups include hydroxymethyl, 2-hydroxyethyl, 2-hydroxypropyl and 3-hydroxypropyl.

"Nitrogen protecting group" means an easily removable group which is known in the art to protect an amino (group against undesirable reaction during synthetic procedures and to be selectively removable. The use of N-protecting groups is well known in the art for protecting groups against undesirable reactions during a synthetic procedure and many such protecting groups are known, CF, for example, T. H. Greene and P. G. M. Wuts, Protective Groups in Organic Synthesis, 2nd edition, John Wiley & Sons, New York (1991), incorporated herein by reference. Representative N-protecting groups include sulfonainides such as methane-sufonyl (Ms), trifluoromethanesulfonyl (Tf), benzenesulfonyl (or pheniylsuilfonvyl), p-toluenesulfonyl (Ts), p-methoxybenzenesulfonyl, phenacylsulfonyl, and the like; carbamates such as methoxycarbonyl, ethoxycarbonyl, 2,2,2-trichloroethoxycarbonyl (Troc), 2-trimethylsilylethyloxycarbonyl (Teoc), tert-butoxycarbonyl (Boc), and the like; amides such as formyl, acetyl, benzoyl, trifluoroacetyl, and the like; N-alkyl derivatives such as benzyl; and N-phosphinyl derivatives such as diphenylphosphinoyl.

In a specific embodiment, the term "about" or "approximately" means within 20%, preferably within 10%, and more preferably within 5% of a given value or range.

Preferred Embodiments

The preparation of N6-substituted adenosine derivatives of formula (1) wherein $X_1$, $X_2$, X, Y, a, Z, P, Q, T, $R_7$ and $R_8$, are defined above is outlined in Scheme 1.

Scheme 1

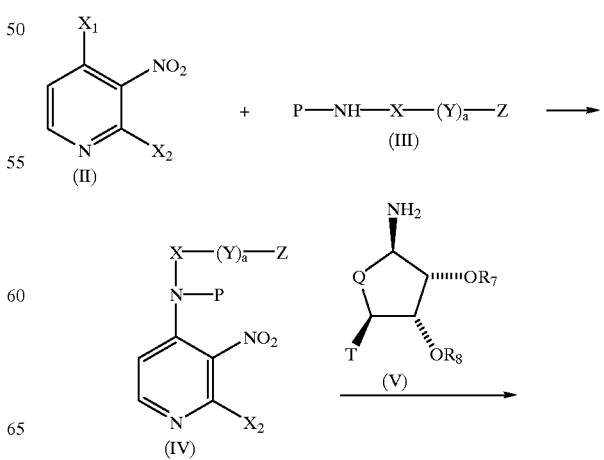

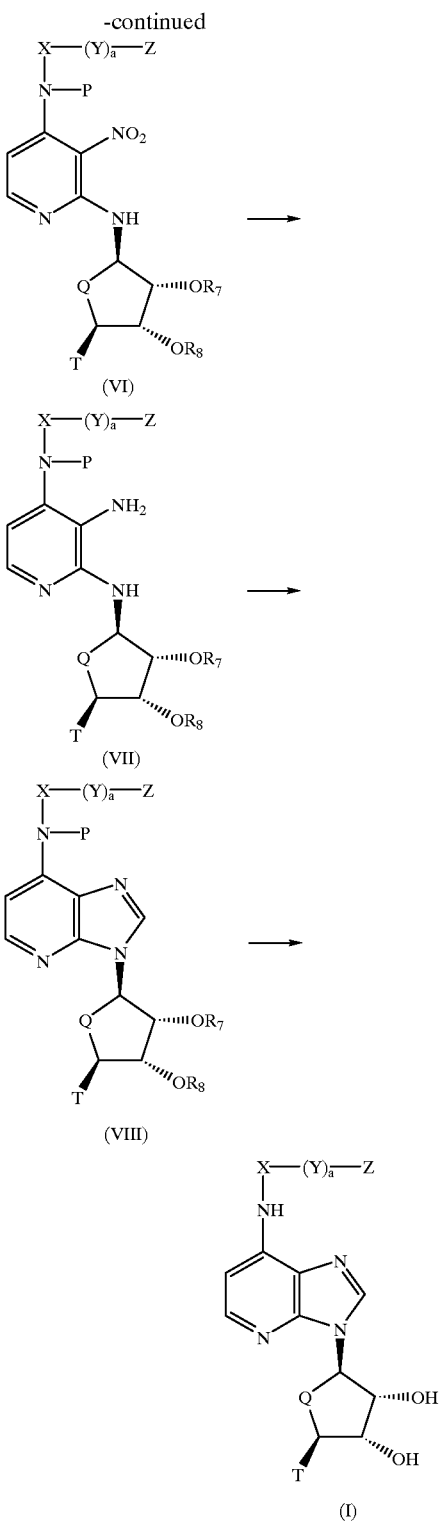

As shown in the foregoing Scheme 1, reaction of the 2,4-dihalo-3-nitropyridine compound (II) and the N-protected amine (III) provides the 2-halo-3-nitro-4-N-protected aminopyridine compound (IV). The reaction is carried out in the presence of an alkoxide such as potassium tert-butoxide or potassium tert-amylate, and the like; an inorganic carbonate base such as potassium carbonate; a metal hydride base such as sodium or potassium hydride; an alkyllithium base such as butyllithium; or a fluoride base such as potassium fluoride. When weaker bases such as potassium carbonate or potassium fluoride are utilized, a crown ether such as 18-crown-6, or a phase transfer catalyst, such as tetrabutyl ammonium bromide may be added to achieve a reasonable rate of conversion. The reaction is carried out in an etheral solvent such as tetrahydrofuran, tert-butyl methyl ether, and the like; an aromatic hydrocarbon solvent such as toluene; or in a polar aprotic solvent such as dimethylformamide, 1-methyl-2-pyrrolidone, dimethylsulfoxide, and the like at a temperature of from about ambient temperature to the reflux temperature of the solvent.

The reaction is preferably accomplished using potassium tert-butoxide in tetrahydrofuran) at about 65 ° C. The product is preferably purified by washing with methanol and heptane.

Alternatively, a metalated version of the protected amine (III) of formula P-NM-X-$(Y)_a$-Z. where M is a metal cation such as Li may be used, in which case use of additional base is unnecessary.

The 2-halo-3-nitro-4-N-protected aminopyridine compound (IV) is then reacted with the protected dihydroxyaminocyclopentane compound (V) in the presence of an inorganic bicarbonate base, such as potassium bicarbonate; a tertiary or aromatic amine base such as 4-methylmorpholiine; an alkoxide such as potassium tert-butoxide or potassium tert-amylate, and the like; an inorganic carbonate base such as potassium carbonate; a metal hydride base such as sodium or potassium hydride; an alkyllithium base such as butyllithium; or a fluoride base such as potassium fluoride, in an ester solvent such as ethyl acetate; an etheral solvent such as tetrahydrofuran, tert-butyl methyl ether, and the like; an aromatic hydrocarbon solvent such as toluene; or a polar aprotic solvent such as dimethylformamide, 1-methyl-2-pyrrolidone, dimethylsulfoxide, and the like, at a temperature of from about ambient temperature to the reflux temperature of the solvent to form the 4-N-protected-2,4-diamino-3-nitiopyridine compound (VI). The reaction is preferably accomplished using potassium carbonate in ethyl acetate at about 80° C.

The protected dihydroxyaminocyclopenitane compound (V) may be utilized as the free base, or as the acid addition salt. Preferred acid addition salts are the trifluoroacetate or benzoate salts.

The reduction of the 4-N-protected-2,4-diamito-3-iiitropyridine compound (VI) to form the 4-N-protected-2,3,4-triiaminopyridine compound (VII) is accomplished using methods well known in the art for the reduction of aromatic nitro compounds such as catalytic hydrogenation using a transition metal catalyst such as platinum. The reduction is also accomplished using a metal such as zinc, iron or tin in the presence of a proton source such as ammonium acetate. Solvents are generally alcohols, or mixtures of non-protic organic solvents such as ethyl acetate or toluene and an alcohol such as methanol. The reduction is preferably accomplished by catalytic hydrogeniationi at about 50 psi of hydrogen in the presence of platinum on carbon, in a mixture of ethyl acetate and methanol at room temperature.

The 4-N-protected-2,3,4-triiaminopyridine compound (VII) is then converted to the N-protected N6-substituted adenosine derivative (VIII) by a reaction with a derivative of formic acid, such as triethyl orthoformate, diethoxymethyl acetate or formamidine acetate, and the like, in a polar aprotic solvent such as dimethylformamide; a higher boiling alcohol such as n-butanol, an ester such as n-butyl acetate; an anhydride suich as acetic anhydride, or an aromatic hydrocarbon such as toluene. Alternatively, the reagent itself (e.g. triethylorthoformate) can be used as the solvent for this reaction. The reaction is optionally catalyzed by an acid such as hydrochloric acid or p-toluenesulfonic acid. The reaction is accomplished at a temperature of from about ambient temperature to the reflux temperature of the solvent. Preferred reaction conditions are triethyl orthoformnate in acetic anhydride at about 120° C.

Removal of the amine protecting group P is accomplished using reagents known in the art for the removal of nitrogen protecting groups. When P is sulfonamido, such as p-toluenesulfonyl, the protecting group is cleaved using a strong acid, such as methanesulfonic acid. hydrochloric acid, trifluoroacetic acid, and the like, or a strong Lewis acid, such as trimethylsilyl trifluoromethanesulfonate in a polar protic solvent such as acetic acid, trifluoroacetic acid, water and the like. A cation scavenger such as thioanisole generally is also employed, resulting in increased purity of the final product. In a preferred aspect of the foregoing process, the groups $R_7$ and $R_8$ together form the dimethyl acetonide. in which case the strongly acidic conditions described above for the removal of P typically also result in hydrolysis of the acetonide. Preferred conditions for removal of the nitrogen protecting group P are trimethylsilyl trifluoroacetate with thioanisole in trifluoroacetic acid at about 70° C.

Alternatively, the tosyl group can be selectively removed by a reductive process using metals such as lithium, sodium, sodium-mercury couple, magnesium and the like. For lithium and sodium, ammonia is typically used as the solvent (dissolving metal reduction). Magnesium reduction is generally carried out in an alcohol such as methanol. The tosyl group might also be removed with a hydride reagent, such as lithium triethylborohydride in an aprotic solvent such as THF, or electrolytically.

In the event that the nitrogen protecting group P is selectively removed, the groups $R_7$ and $R_8$ are then removed using techniques known in the art forremoval of hydroxyl protecting grotups. When $R_7$ and $R_8$ together form the dimethyl acetonide, the acetonide is hydrolyzed usinig an acid such as hydrochloric acid or trifluoroacetic acid, in a protic solvent such as water or an alcohol; or an organic solvent such as tetrahydrofuran can also be used. Acetonide hydrolysis is preferably accomplished usinig a mixture of aqueous concentrated hydrochloric acid and tetrahydrofuran at a temperature ranging from ambient temperature to about 35° C.

In a preferred aspect of the foregoing process,

Q is $CH_2$;

T is

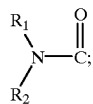

X is a straight or branched chain alkylene;

a=0;

Z is

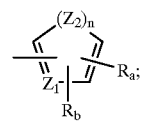

$Z_1$ is N, $CR_5$, $(CH)_m$-$CR_5$ or $(CH)_m$-N, m being 1 or 2;

$Z_2$ is N, $NR_6$, O or S; n is 0 or 1;

$R_1$, $R_2$, $R_3$, $R_4$, $R_5$ and $R_6$ are independently H or alkyl;

$R_7$ and $R_8$ are independently hydrogen or alkyl, or $R_7$ and $R_8$ together may form

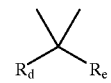

where $R_d$ and $R_e$ are independently hydrogen or alkyl, or together with the carbon atom to which they are attached may form a 1,1-cycloalkyl group; and $R_a$ and $R_b$ are independently H, OH, alkyl, hydroxyalkyl, alkyl mercaptyl, thioalkyl, alkoxy, alkyoxyalkyl, amino, alkyl amino, carboxyl, acyl, halogen, carbamoyl, alkyl carbamoyl, aryl or heterocyclyl.

In a more preferred aspect of the foregoing process, P is selected from the group consisting of sulfonamides, carbamates, amides, N-alkyl derivatives and N-phosphinyl derivatives.

In a still more preferred aspect of the foregoing process, P is a sulfonamide derivative.

In a still yet more preferred aspect of the foregoing process, P is o-toluenesulfonyl.

A process for preparing [1S-[1α,2β,3β,4α(S*)]]-4-[7-[[1-[(3-chlorothien-2-yl)methyl]propyl]amino]-3 H-imidazo[4,5-b]pyrid-3-yl]N-ethyl 2,3-dihydroxycyclopentanecarboxamide (XV) is shown in Scheme 2.

Scheme 2

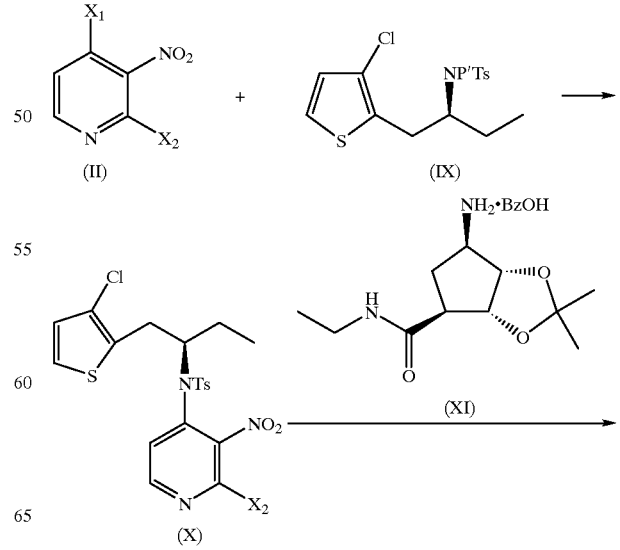

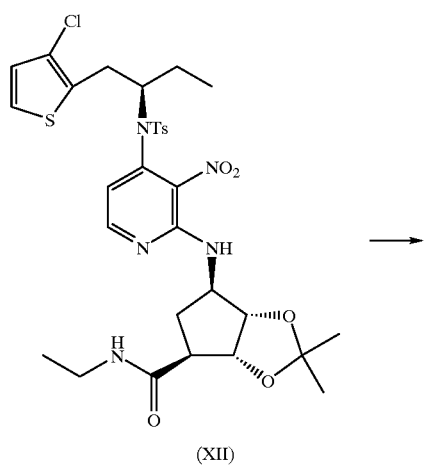

(XII)

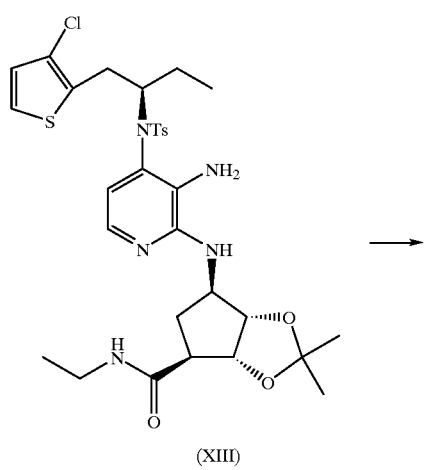

(XIII)

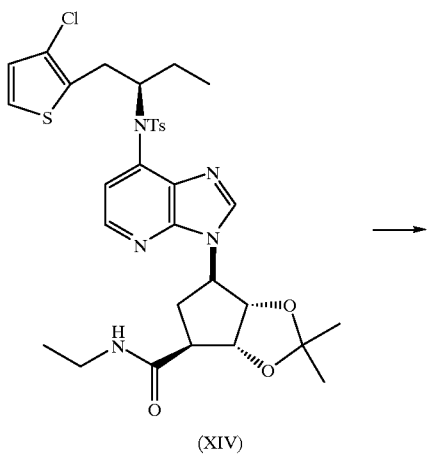

(XIV)

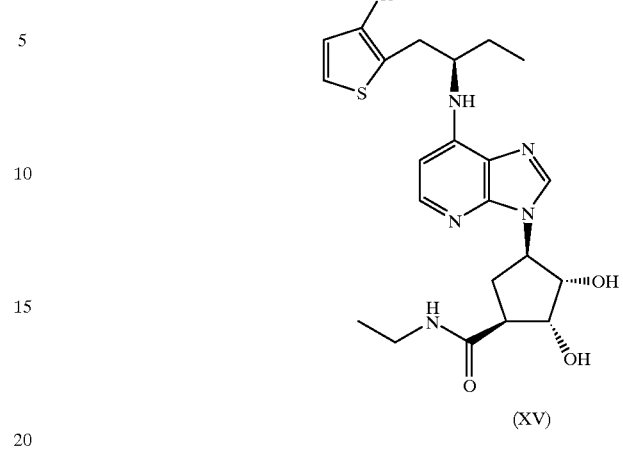

(XV)

As shown in the foregoing Scheme 2, 2,4-dihalo-3-nitropyridine (II) ($X_1$=F, $X_2$=Cl or F) is reacted with the (R)-N-[1-[(3-chlorothien-2-yl)methyl]propyl]-4-methylbenzesulfonamide compound (IX) to form the (R)-N-[1-[3-chlorothien-2-yl)methyl]propyl]-N-(2-halo-3-nitropyrid-4-yl)-4-methylbenzenesulfonamide compound (X) ($X_2$=Cl or F).

When P' is H, the reaction is performed by deprotonation of the secondary amine by reaction with base, preferably potassium tert-butoxide in tetrahydrofuran at a temperature of about 0° C. to about ambient temperature, followed by addition of the 2,4-dihalo-3-nitropyridine compound and heating at about 65° C. When P' is Li, no additional base is required and the reaction of (II) and (IX) is preferably performed in refluxing 1-methyl-2-pyrrolidinone or toluene.

In one preferred aspect of the foregoing, the 2,4-dihalo-3-nitropyridine compound (II) is 2,4-difluoro-3-nitropyridine, which is prepared by reaction of 2,4-diclhoro-3-nitropyridine with a nucleophilic fluoride reagent, preferably KF. Incomplete reaction of 2,4-dichloro-3-nitropyridine with the nucleophilic fluoride reagent results in formation of a mixture of 2,4-difluoro-3-nitropyridine and 2-chloro-4-fluoro-3-nitropyridine. Use of this mixture for reaction with the (R)-N-[1-[(3-chlorothien-2-yl)methyl]propyl]-4-methylbenzenesulfoniamide, compound (IX), results in formation of the (R)-N-[1-[3-chlorothien-2-yl)methyl]propyl]-N-(2-halo-3-nitropyrid-4-yl)-4-methylbenzenesulfonamide, compound (X), wherein halo is a mixture of Cl and F.

The (R)-N-[1-[3-chlorothien-2-yl)methyl]propyl]-N-(2-halo-3-nitropyrid-4-yl)-4-methylbenzenesulfonamide, compound (X), is then reacted with 3aR-[3aα,4α, 6a,6aα]-6-amino-N-ethyltetrahydro-3,3-dimethyl-2,4-dioxabicyclo[3.3.0]octan-8-carboxamide, benzoate (XI), to form [3aR-[3aα,4α, 6a(R*),6aα]]-6-[4-[[1-[(3-chlorothien-2-yl)methyl]propyl][4-methylbenzenesulfonyl]amino]-3- nitropyrid-2-ylamino]N-ethyltetrahydro-2,2-dimethyl-4H-cyclopenta-1,3-dioxole-4-carboxamide (XII). The reaction is preferably accomplished using excess alkoxide base, preferably potassium carbonate, at about 80° C. in an organic solvent such as ethyl acetate or 1-methyl-2-pyrrolidinone. 1-methyl-2-pyrrolidinone is the preferred solvent when halo is a mixture of Cl and F. The preparation of 3aR-[3aα,4α, 6a,6aα]-6-amino-N-ethyltetrahydro-3,3-dimethyl-2,4-dioxabicyclo[3,3,0]octane-8-carboxamide, benzoate is described in U.S. Pat. Nos. 5,808,093, 5,670,649 and 5,684,159, the contents of which are hereby incorporated herein by reference.

Reduction of [3aR-[3aα,4α, 6a(R*),6aα]]-6-[4-[[1-[(3-chlorothien-2-yl)methyl]propyl][4-methylbenzenesulfonyl]amino]-3-nitropyrid-2-ylamino]N-ethyltetrahydro-2,2-dimethyl-4H-cyclopenta-1,3-dioxole-4-carboxamide (XII) to form [3aR-[3aα,4α, 6a(R*),6aα]]-6-[4-[[1-[(3-chlorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide (XIII) is then accomplished as described in Scheme 1 above, preferably by catalytic hydrogenation at about 50 to about 55 psi of hydrogen in the presence of catalytic platinum on carbon in a mixture of ethyl acetate and methanol at about ambient temperature.

Cyclization of [3aR-[3aα,4α,6a(R*),6aα]]-6-[4-[[1-[(3-chlorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide (XIII) to form [3aR-[3aα,4α,6a(R*),6aα]]-6-[7-[[1-[(3-chlorothien-2-yl)methyl]propyl][4-methylbenzenesulfonyl]amino]-3H-imidazo[4,5-b]pyrid-3-yl]N-ethyl tetrahydro-2,2-dimethyl-4H-cyclopenta-1,3-dioxole-4-carboxamide (XIV) is then accomplished as described in Scheme 1 above.

Conversion of [3aR-[3aα,4α, 6a(R*),6aα]]-6-[7-[[1-[(3-chlorothien-2-yl)methyl]propyl][4-methylbenzenesulfonyl]amino]-3H-1imidazo[4,5-b]pyrid-3-yl]N-ethyltetrahydro-2,2-dimethyl-4H-cyclopenta-1,3-dioxole-4-carboxamide (XIV) to [1S-[1β,2β,3β,4β(S*)]]-4-[7-[[1-[(3-chlorothien-2-yl)methyl]propyl]amino]- 3H-imidazo[4,5-b]pyrid-3-yl] N-ethyl 2,3-dihydroxycyclopentanecarboxamide (XV) is accomplished by the simultaneous or sequential removal of the toluenesulfonyl group and the dimethyl acetonide as described in Scheme 1 above.

Selective removal of the toluenesulfonyl group is preferably accomplished using magnesium metal in a mixture of methanol and toluene at about 40° C. or using a hydride reagent such as lithium triethylborohydride in tetrahydrofuranat about 0° C. The dimethyl acetonide is then hydrolyzed using an acid such as hydrochloric acid or trifluoroacetic acid, in a protic solvent such as water or an alcohol or an organic solvent such as tetrahydrofuran. Acetonide hydrolysis is preferably accomplished using a mixture of aqueous concentrated hydrochloric acid and tetrahydrofuran at ambient temperature to about 35° C.

Simultaneous removal of the toluenesulfonyl group and hydrolysis of the acetonide is accomplished using a strong acid, such as methanesulfonic acid, hydrochloric acid, trifluoroacetic acid, and the like, or a strong Lewis acid. such as trimethylsilyl trifluoromethanesulfonate in a polar protic solvent such as acetic acid, trifluoroacetic acid, water and the like. A cation scavenger such as thioanisole generally is also employed, resulting in increased purity of the final product. Simultaneous removal of the toluenesulfonyl group and the dimethyl acetonide is accomplished by heating a mixture of [3aR-[3aα,4α,6a(R*),6aα]]-6-7-[[1-[3-[(3-chlorothien-2-yl)methyl]propyl][4-methylbenzenesulfonyl]amino]-3H-imidazo[4,5-b]pyrid-3-yl]N-ethyl tetrahydro-2,2-dimethyl-4H-cyclopenta-1,3-dioxole-4-carboxamide and trimethylsilyl trifluoroacetate in trifluoroacetic acid/toluene at about 70° C. or by heating a mixture of [3aR-[3aα,4α, 6a(R*),6aα]]-6-[7-[[1-[(3-chlorothien-2-yl)methyl]propyl][4-methylbenzenesulfonyl]amino]-3H-imidazo[4,5-b]pyrid-3-yl]N-ethyl tetrahydro-2,2-dimethyl-4H-cyclopenta-]1,3-dioxole-4-carboxamide, methanesulfonic acid and thioanisole in trifluoroacetic acid at about 85° C.

In another aspect, this invention is directed to a process for preparing [3aR-[3aα,4α,6a(R*),6aα]]-6-[7-[[1-[(3-chlorothien-2-yl)methyl]propyl][4-methylbenzenesulfonyl]amino]-3H-imidazo[4,5-b]pyrid-3-yl]N-ethyl tetrahydro-2,2-dimethyl-4H-cyclopenta-1,3-dioxole-4-carboxamide comprising (i) reacting (R)-N-[1-[3-chlorothien-2-yl)methyl]propyl]-N-(2-fluoro-3-nitropyrid-4-yl)-4-methylbenzenesulfonamide with 3aR-[3aα,4α,6a,6aα]-6-amino-N-ethyltetrahydro-3,3-dimethyl-2,4-dioxabicyclo[3.3.0]octan-8-carboxamide, benzoate to form [3aR-[3aα,4α,6a(R*),6aα]]-6-[4-[[1-[(3-chlorothien-2-yl)methyl]propyl][4-methylbenzenesulfonyl]amino]-3-nitropyrid-2-ylamino]N-ethyl tetrahydro-2,2-dimethyl-4H-cyclopenta-1,3-dioxole-4-carboxamide, (ii) reducing the [3aR-[3aα,4α,6a(R*),6aα]]-6-[4-[[1-[(3-chlorothien-2-yl)methyl]propyl][4-methylbenzenesulfonyl]amino]-3-nitropyrid-2-yl amino]N-ethyl tetrahydro-2,2-dimethyl-4H-cyclopenta-1,3-dioxole-4-carboxamide prepared in step (i) to form [3aR-[3aα,4α,6a(R*),6aα]]-6-[4-[[1-[(3-chlorothien- 2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide and (iii) reacting the [3aR-[3aα,4α,6a(R*),6aα]]-6-[4-[[1-[(3-chlorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide prepared in step 2 above with an orthoformate ester, formamidine acetate or dimethylformamide dimethyl acetal, wherein steps (i)–(iii) are performed in a concatenated fashion without purification of the intermediate compounds, [3aR-[3aα,4α,6a(R*),6aα]]-6-[4-[[1-[(3-chlorothien-2-yl)methyl]propyl][4-methylbenzenesulfonyl]amino]-3-nitropyrid-2-ylamino]N-ethyl tetrahydro-2,2-dimethyl-4H-cyclopenta-1,3-dioxole-4-carboxamide and [3aR-[3aα,4α,6a(R*),6aα]]-6-[4-[[1-[(3-chlorothien-2-yl)methyl]propyl][4-methylbenzenesulfonyl]amino-3-aminopyrid-2-ylamino]N-ethyl tetrahydro-2,2-dimethyl-4H-cyclopenta-1,3-dioxole-4-carboxamide.

For example, (R)-N-[1-[-chlorothien-2-yl)methylpropyl]-N-(2-fluoro-3-nitropyrid-4-yl)-4-methylbenzenesulfonamide and 3aR-[3aα,4α,6a,6aα]-6-amino-N-ethyltetrahydro-3,3-dimethyl-2,4-dioxabicyclo[3.3.0]octan-8-carboxamide, benzoate and potassium carbonate are heated in ethyl acetate to form an ethyl acetate solution of [3aR-[3aα,4α,6a(R*),6aα]]-6-[4-[[1-[(3-chlorothien-2-yl)methyl]propyl][4-methylbenzenesulfonyl]amino]-3-nitropyrid-2-ylamino]N-ethyl tetrahydro-2,2-dimethyl-4H-cyclopenta-1,3-dioxole-4-carboxamide. The ethyl acetate solution is washed with water and brine to remove water-soluble impurities and then the ethyl acetate solution is diluted with methanol, a platinum catalyst is added and the mixture is hydrogenated under about 50 psi of hydrogen to give a solution in ethyl acetate/methanol of [3aR-[3aα,[4α,6a(R*),6aα]]-6-[4-[[1-[(3-chlorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide. The catalyst is filtered off, the filtrate is concentrated, and triethyl orthoformate and acetic anhydride are added to the crude [3aR-[3aα,4α,6a(R*),6aα]]-6-[4-[[1-[(3-chlorothien-2-yl)methyl]propyl [4-methylbenzenesulfonyl]amino]-3-aminopyrid-2-ylamino]N-ethyl tetrahydro-2,2-dimethyl-4H-cyclopenta-1,3-dioxole-4-carboxamide. Heating of the mixture effects conversion to [3aR-[3aα,4α,6a(R*),6aα]]-6-[7-[[1-[(3-chlorothien-2-yl)methyl]propyl][4-methylbenzenesulfonyl]amino]-3H-imidazo[4,5-b]pyrid-3-yl]N-ethyl tetrahydro-2,2-dimethyl-4H-cyclopenta-1,3-dioxole-4-carboxamide, which is isolated by crystallization, preferably using 2-propanol.

In another aspect, this invention is directed to a process for preparing (R)-N-[1-[3-chlorothien-2-yl)methyl]propyl]-N-(2-)halo-3-nitropyrid-4-yl)-4-methylbenzenesulfonamide, wherein halo is Cl or F, comprising
(i) reacting 2,4-dichloro-3-nitropyridine with a fluorinating agent to form 2,4-difluoro-3-nitropyridine or a mixture of 2,4-difluoro-3-nitropyridine and 2-chloro-4-fluoro-3-nitropyridine and
(ii) reacting the product of step (i) with (R)-N-[1-[(3-chlorothien-2-yl)methyl]propyl]-4-methylbenzenesulfonamide lithium salt or (R)-N-[1-[(3-chlorothien-2-yl)methyl]propyl]-4-methylbenzenesulfonamide, wherein steps (i) and (ii) are performed in a concatenated fashion without isolation of the product of step (i).

For example, heating a mixture of 2,4-dichloro-3-nitropyridine with KF and catalytic tetrabutylammonium bromide in toluene or toluene/1-methyl-2-pyrrolidinone results in the formation of a solution of 2,4-difluoro-3-nitropyridine. (R)-N-[1-[(3-chlorothien-2-yl)inethyl]propyl]-4-methylbenzenesulfonamide lithium salt is then added to the solution and the mixture is heated to effect conversion to the (R)-N-[1-[3-chlorothien-2-yl)methyl]propyl]-N-(2-fluoro-3-nitropyrid-4-yl)-4-methylbenzesulfonamide, which is isolated by crystallization, preferably by aqueous extraction of the reaction mixture followed by addition of a hydrocarbon solvent such as heptane to the organic solution.

In another aspect of the foregoing process, excess KF is utilized, which acts as the fluorinating agent in the first step and the base in the second step, thereby making it possible to utilize (R)-N-(1-[(3-chlorothien-2-yl)methyl]propyl]-4-methylbenzenesulfonamide rather than the lithium salt.

In another aspect, this invention is directed to a process for preparing [3aR-[3aα,4α,6a(R*),6aα]]-6-[7-[[1-[(3-chlorothien-2-yl)methyl]propyl][4-methylbenzenesulfonyl]amino]-3H-imidazo[4,5-b]pyrid-3-yl]N-ethyl tetrahydro-2, 2-dimethyl-4H-cyclopenta-1,3-dioxole-4-carboxamide comprising
(i) reacting 2,4-diclhoro-3-nitropyridine with a fluorinating agent to form 2,4-difluoro-3-nitropyridine,
(ii) reacting the 2,4-difluoro-3-nitropyridine with (R)-N-[1-[(3-chlorothien-2-yl)methyl]propyl]-4-methylbenzenesulfonamide lithium salt or (R)-N-[1-[(3-chlorothien-2-yl)methyl]propyl]-4-methylbenzenesulfonamide to form (R)-N-[1-[3-chlorothien-2-yl)methyl]propyl]-N-(2-fluoro-3-nitropyrid-4-yl)-4-methylbenzenesulfonylamide, (iii) reacting the (R)-N-[1-[3-chlorothien-2-yl)methyl]propyl]-N-(2-fluoro-3-nitropyrid-4-yl)-4-methylbenzenesulfonamide with 3aR-[3aα,4α,6a, 6aα]-6-amino-N-ethyltetrahydro-3,3-dimethyl-2,4-dioxabicyclo [3.3.0)octan-8-carboxamide, benzoate to form [3aR-[3aα,4α,6a(R*),6aα]]-6-[4-[[1-[(3-chlorothien-2-yl)methyl]propyl][4-methylbenzenesulfonyl]amino]-3-nitropyrid-2-ylamino]N-ethyl tetrahydro-2,2-dimethyl-4H-1-cyclopenta-1,3-dioxole-4-carboxamide, (iv) reducing the [3aR-[3aα,4α,6a(R*),6aα]]-6-[4-[[1-[(3-chlorothien-2-yl)methyl]propyl][4-methylbenzenesulfonyl]amino]-3-nitropyrid-2-ylamino]N-ethyl tetrahydro-2,2-dimethyl-4H-cyclopenta-1,3-dioxole-4-carboxamide prepared in step (i) to form [3aR-[3aα,4α,6a(R*),6aα]]-6-[4-[[1-[(3-chlorothien-2-yl)methyl]propyl][4-methylbenzenesulfonyl]amino]-3-aminopyrid-2-ylamino]N-ethyl tetrahydro- 2,2-dimethyl-4H-cyclopenta-1,3-dioxole-4-carboxamide and (v) reacting the [3aR-[3aα,4α,6a(R*),6aα]]-6-[4-[[1-[(3-chlorothien-2-yl)methyl]propyl][4-methylbenzenesulfonyl]amino]-3-aminopyrid-2-ylamino N-ethyl tetrahydro-2,2-dimethyl-4H-cyclopenta-1,3-dioxole-4-carboxamide with an orthoformate ester, formamidine acetate or dimethylformamide dimethyl acetal wherein steps (i)–(v) are performed in a concatenated fashion without purification of the intermediate compounds 2,4-difluoro-3-nitropyridine, (R)-N-[1-[3-chlorothien-2-yl)methyl]propyl]-N-(2-halo-3-nitropyrid-4-yl)-4-methylbenzesulfonamide, [3aR-[3aα,4α,6a(R*),6aα]]-6-4-[[1-[(3-yl)methyl]propyl][4-methylbenzenesulfonyl]amino]-3-nitropyrid-2-ylamino]N-ethyl tetrahydro-2,2-dimethyl-4H-cyclopenta-1,3-dioxole-4-carboxamide and [3aR-[3aα,4α,6a(R*),6aα]]-6-[4-[[1-[(3-chlorothien-2-yl)methyl)propyl][4-methylbenzenesulfonyl]amino]-3-aminopyrid-2-ylamino]N-ethyl tetrahydro-2,2-dimethyl-4H-cyclopenta-1,3-dioxole-4-carboxamide, wherein the concatenation is effected by combining the concatenated processes described above.

In another aspect, this invention is directed to a compound of formula (XVI)

(XVI)

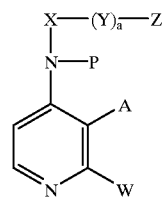

wherein

A is NH$_2$ or NO$^2$;

P is a nitrogen protecting group;

W is Cl, F or a group of formula

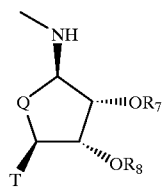

Q is CH$_2$ or O;
T is

or R$_3$O—CH$_2$;
X is a straight or branched chain alkylene, cycloalkylene or cycloalkylene group;
Y is NR$_4$, O or S;
a=0 or 1;

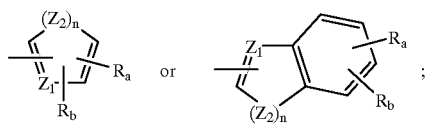

Z is of the formula
Z$_1$ is N, CR$_5$, (CH)$_m$-CR$_5$ or (CH)$_m$-N, m being 1 or 2;
Z$_2$ is N, NR$_6$, O or S;
n is 0 or 1;
R$_1$, R$_2$, R$_3$, R$_4$, R$_5$ and R$_6$ are independently H, alkyl, aryl or heterocyclyl;
R$_7$ and R$_8$ are independently H, alkyl, aralkyl, carbamoyl, alkyl carbamoyl, dialkylcarbamoyl, acyl, alkoxycarbonyl, aralkoxycarbonyl, or aryloxycarbonyl, or R$_7$ and R$_8$ together may form

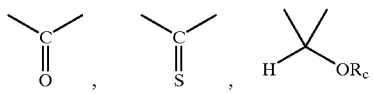

where R$_c$ is hydrogen or alkyl,

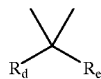

where R$_d$ and R$_e$ are independently hydrogen, alkyl, or R$_d$ and R$_e$ together with the carbon atom to which they are attached may form a 1,1-cycloalkyl group; and
R$_a$ and R$_b$ are independently H, OH, alkyl, hydroxyalkyl, alkyl mercaptyl, tiloalkyl, alkoxy, alkyoxyalkyl, amino, alkyl amino, carboxyl, acyl, halogen, carbamoyl, alkyl carbamoyl, aryl or heterocyclyl, which compound is a useful intermediate in the preparation of N-protected N6-substituted adenosine compounds using the processes described herein.

Preferred compounds have formula (XVI) wherein P is selected from sulfonamides, carbamates, amides, N-alkyl derivatives and N-phosphinyl derivatives.

More preferred compounds have formula (XVI) wherein P is sulfonamido.

Still more preferred compounds: have formula (XVI) wherein
P is sulfonamido;
Q is CH$_2$;

T is R$_2$
X is a straight or branched chain alkylene;
a=0;
Z is

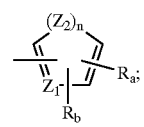

Z$_1$ is N, CR$_5$, (CH)$_m$—CR$_5$ or (CH)$_m$-N, m being 1 or 2;
Z$_2$ is N, NR$_6$, O or S, n being 0 or 1;
R$_1$, R$_2$, R$_5$ and R$_6$ are independently H or alkyl;
R$_7$ and R$_8$ are alkyl, or R$_7$ and R$_8$ together may form

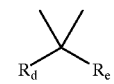

where R$_d$ and R$_e$ are independently hydrogen or alkyl, or together with the carbon atom to which they are attached may form a 1,1-cycloalkyl group; and
R$_a$ and R$_b$ are independently H, OH, alkyl, hydroxyalkyl, alkyl mercaptyl, thioalkyl, alkoxy, alkyoxyalkyl, amino, alkyl amino, carboxyl, acyl, halogen, carbamoyl, alkyl carbamoyl, aryl or heterocyclyl.

Representative still more preferred compounds include, but are not limited to 3aR-[3aα,4α,6a(R*),6aα]]-6-[4-[[1-[(3-chlorothien-2-yl)methyl]propyl][4-methylbenzenesulfonyl]amino]-3-nitropyrid-2-ylamino]N-ethyl tetrahydro-2,2-dimethyl-4H-cyclopenta-1,3-dioxole-4-carboxamide: [3aR-[3aα,4α,6a(R*),6aα]]-6-[4-[[1-[(3-chlorothien-2-yl)methyl]propyl][4-methylbenzenesulfonyl]-3-aminopyrid-2-ylamino]N-ethyl tetrahydro-2,2-dimethyl-4H-cyclopenta-1,3-dioxole-4-carboxamide; and [3aR-[3aα,4α,6a(R*),6aα]]-6-[7-[[1-[(3-chlorothien-2-yl)methyl]propyl][4-methylbenzenesulfonyl]amino]-3H-imidazo[4,5-b]pyrid-3-yl]N-ethyl tetrahydro-2,2-dimethyl-4H-cyclopenta-1,3-dioxole-4-carboxamide.

The foregoing may be better understood by reference to the following examples, which are presented for purposes of illustration and are not intended to limit the scope of the invention.

EXAMPLE 1

Preparation of (R)-N-[1-[(3-chlorothien-2-yl)methyl] propyl]-4-methylbenzenesulfonamide.

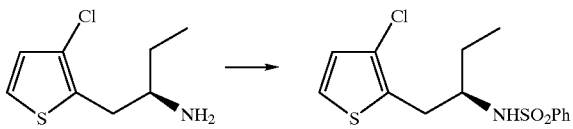

Five grams of 3-chloro-2-(2-aminobutyl)thiophene is dissolved in 10 ml of methylene chloride in a 3-neck round bottomed flask blanketed with an inert atmosphere at 0° C. Pyridine (2.2 ml) is added in one portion followed by 3.37 ml of benzenesulfonyl chloride. The latter reagent is added at such a rate as to allow the methylene chloride solution to warm to 15° C. After warming to ambient temperature, the mixture is stirred for 4 hours and diluted with 100 ml of diethyl ether. The solution is poured into a separatory funnel and washed with water, dilute 1N HCl, saturated aqueous sodium bicarbonate and brine. The organic phase is dried over magnesium sulfate, filtered and concentrated in vacuo to provide (R)-N-[1-[(3-chlorothien-2-yl)methyl]propyl]-4-methylbenzenesulfonamide (6.7 g) as an orange oil. MS: m/z (E1, 70EV) 330 (20%). $^1$H NMR (200 MHz; CDCl$_3$): δ 0.82 (3H, t, CH$_3$); 1.6 (2H, m, CH$_2$), 2.85 (2H, d, CH$_2$), 3.45 (1H, m, CH), 6.8 (1H, d, CH), 7.1 (1H, d, C H), 7.4–8.2(5H, m, Ph).

EXAMPLE 2

Alternate preparation of (R)-N-[1-[(3-chlorothien-2-yl)methyl]propyl]-4-methylbenzenesulfonamide.

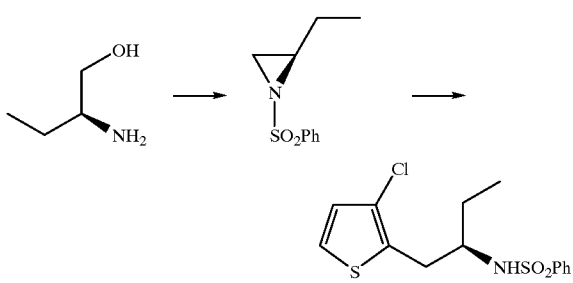

Step 1: Four grams of 2-(R)-aminobutanol and 7.2 grams of NaOH are suspended in toluene in a round bottom flask at ambient temperature. Benzenesulfonyl chloride (16.7 g) is added with agitation in one portion. The resulting white suspension is heated at 62° C. for 6 hours. Water (90 mL) is added and the layers are separated. The organic layer is washed with 70 ml of water, dried over magnesium sulfate and concentrated to provide 1-benzenesulfonyl-2(R)-ethylaziridine (6.7 g) as a colorless oil which is purified by flash chromatography over silica gel. MS: m/z (E1, 70EV) 212 (20%)

Step 2: The 1-benzenesulfonyl-2(R)-ethylaziridine is opened with 2-lithio-3-chlorothiophene to generate benzene sulfonyl protected chlorothienylbutylamine as described in PCT/US97/15729. $^1$H NMR (200 MHz; CDCl$_3$): δ 0.82 (3H, t, CH$_3$), 1.6 (2H, m, CH$_2$), 2.85 (2H, d, CH$_2$), 3.45 (1H, m, CH), 6.8 (1H, d, CH), 7.1 (1H, d, CH), 7.4–8.2 (5H, m, Ph).

EXAMPLE 3

Preparation of (R)-N-[1-[(3-chlorothien-2-yl)methyl]propyl]-4-bromobenzenesulfonamide.

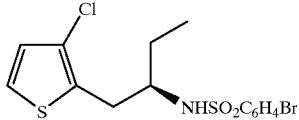

Five grams of 3-chloro-2-(2-aminobutyl)thiophene is dissolved in 10 ml of methylene chloride in a 3-neck round bottomed flask blanketed with an inert atmosphere at 0° C. Pyridine (2.2 ml) is added in one portion followed by 6.74 g of 4-bromobenzenesulfonyl chloride which had been previously dissolved in 10 ml of methylene chloride. After the addition is complete, the mixture is stirred at ambient temperature for 3 hours and then at reflux for 2 hours. Two equivalents of triethylamine are added and the mixture is allowed to stir for 14 hours at ambient temperature before diluting with 100 ml of diethyl ether. The solution is poured into a separatory funnel and washed with water, dilute 1N HCl, saturated aqueous sodium bicarbonate and brine, dried over magnesium sulfate, filtered and concentrated in vacuo to provide (R)-N-[1-[(3-chlorothien-2-yl)methyl]propyl]-4-bromobenzenesulfonamide (8.3 g) as an orange oil which solidifies on standing. MS: m/z (E1, 70EV) 410 (15%). $^1$H NMR (200 MHz; CDCl$_3$): δ 0.9 (3H, t, CH$_3$), 1.6 (2H, m, CH$_2$), 2.85 (2H, d, CH$_2$), 3.45 (1H, m, CH), 6.75 (1H, d, CH), 7.1 (1H, d, CH), 7.4–7.8 (4H, m, Ph).

EXAMPLE 4

Preparation of (R)-N-[1-[(3-chlorothien-2-yl)methyl]propyl]-4-nitrobenizenesulfonamide.

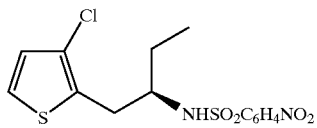

Six grams of 3-chloro-2-(2-aminobutyl)thiophene is dissolved in 10 ml of methylene chloride in a 3-neck round bottomed flask blanketed with an inert atmosphere at 0° C. Triethylamine (6.6 ml) is added in one portion followed by 7.8 g of 4-nitrobenzenesulfonyl chloride which had been previously dissolved in 10 ml of methylene chloride. After stirring for 1 hour at ambient temperature, the methylene chloride is removed under vacuum and 40 ml of methanol is added with warming to dissolve all solids. The resulting solution is poured into cold water, agitated for 30 minutes, filtered and washed with cold water, and the isolated material is dried in a vacuum oven to provide (R)-N-[1-[(3-chlorothien-2-yl)methyl]propyl]-4-nitrobenzenesulfonamide (11.3 g) as a tan solid. MS: m/z (E1, 70EV) 375(10%). $^1$H NMR (200 MHz; CDCl$_3$): δ 0.95 (3H, t, CH$_3$), 1.7 (2H, m, CH$_2$), 2.85 (2H, m, CH$_2$), 3.5 (1H, m, CH), 6.65 (1H, d, CH), 7.0 (1H, d, CH), 7.9 (2H, d, Ph), 8.2 (2H, d, Ph).

EXAMPLE 5

Preparation of (R)-N-[1-[(3-chlorothien-2-yl)methyl]propyl]methanesulfonamide.

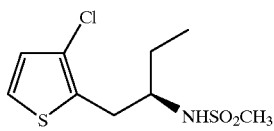

Five grams of 3-chloro-2-(2-aminobutyl)thiophene is dissolved in 10 ml of methylene chloride in a 3-neck round bottomed flask blanketed with an inert atmosphere at 0° C. Pyridine (2.2 ml) is added in one portion followed by 2.05 ml of methanesulfonyl chloride. After warming to room temperature, the mixture is stirred for 4 hours before diluting with 100 ml of diethyl ether. The solution is poured into a separatory funnel and washed with water, dilute 2N HCl, saturated aqueous sodium bicarbonate and brine, dried over magnesium sulfate, filtered and concentrated in vacuo to provide (R)-N-[1-[(3-chlorothien-2-yl)methyl]propyl]methanesulfonamide (5.5 g) as an orange oil which solidifies upon standing in a refrigerator overnight. MS: m/z (EI, 70EV) 267 (5%). $^1$H NMR (200 MHz; CDCl$_3$): δ 1.0 (3H, t, CH$_3$), 1.6 (2H, m, CH$_2$), 2.65 (3H, s, CH$_3$), 3.0 (2H, m, CH$_2$), 3.6 (1H, m, CH), 6.9 (1H, d, CH), 7.2 (1H, d, CH).

EXAMPLE 6

Preparation of 2,4-difluoro-3-nitropyridine.

2,4-Difluoro-3-nitropyridine is prepared by modification of the procedure of Kroon et al., *Recl. Trav. Chim. Pay-Bas* 95: 127, 1976 as described below.

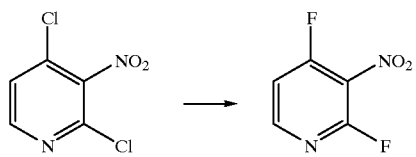

Method A

A reaction vessel is charged with 1 eq. of 2,4-dichloro-3-nitropyridine. 3.5 eq. of KF, 0.05 eq. of 18-crown-6 and 1-methyl-2-pyrrolidinone. The mixture is heated to 100° C. for 15 hours and then cooled to 22° C. Ethyl acetate is added to the reaction vessel and the mixture stirred for 15 minutes. The mixture is washed with water and then with brine. The ethyl acetate layer is dried with magnesium sulfate and the ethyl acetate removed under reduced pressure to provide the title compound.

Method B

A mixture of 300 g (1.56 mol. 1 eq.) of 2,4-dichloro-3-nitropyridine, 1.0 L of 1-methyl-2-pyrrolidinone, 270.5 g (4.65 mol, 2.97 eq.) of potassium fluoride and 66.0 g (0.25 mol. 0.16 eq.) of 18crown-6 is heated with stirring at 100° C. for 2 hours. The reaction mixture is cooled to 20° C. and 1.75 L of water is added. The mixture is stirred until the inorganic salts are dissolved. 1.75 L of tert-butyl methyl ether (TMBE) is added. The mixture is stirred and the layers are separated. The organic layer is washed with 300 ml of brine and dried over magnesium sulfate. The organic layer is then concentrated under reduced pressure. 2,4-Difluoro-3-nitro-pyridine (208 g, 83% yield) is obtained as a brown oil with a purity of 97 A% (HPLC). The oil may be used as is or distilled. 42.61 g of the 2,4-difluoro-3-nitropyridine is distilled at 61–64° C. at 4.0 torr to give the title compound (38.15 g, 90% yield., 99.6 A% (HPLC)) as a colorless oil. $^1$H NMR (200 MHz, CDCl$_3$): δ 8.45 (1H, ap. t), 7.28 (1H, dd). MS (EI, 70 eV, relative intensity): 160 (M$^-$, 75), 114 (25).

Alternatively, the reaction may be performed with 0.3 eq. of tetrabutyl ammonium bromide, in place of 18-crown-6, in toluene at 110° C.

EXAMPLE 7

Preparation of (R)-N-[1-[(3-chlorothien-2-yl)methyl]propyl]-4-methylbenzenesulfonamide.

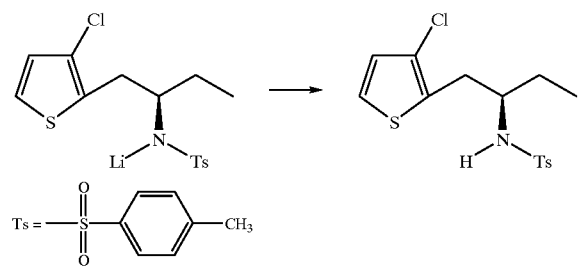

A mixture of 50.0 g (0.143 mol) of (R)-N-[1-[(3-chlorothien-2-yl)methyl]propyl]-4-methylbenzenesulfonamide lithium salt, prepared as described in PCT/US97/15729, in 50 g methanol is heated with stirring at 65° C. until dissolution of the solids is completed. The solution is cooled to 60° C. and 85 g water is added to the mixture dropwise. The mixture is stirred for 1.5 hours and then cooled to 20° C. The solids are isolated by filtration. Drying under vacuum with nitrogen bleed affords 46.6 g (95%) of the free base (R)-N-[1-[(3-chlorothien-2-yl)methyl]propyl]-4-methylbenzenesulfonamide.

HPLC A% is 99.74 A%. water content (by Karl Fisher analysis) 0.2%, Mμ.: 68–70° C. MS (EI, 70 eV): 344/346 (M$^-$, 20), 212 (100). $^1$H NMR (200 MHz, CDCl$_3$): δ 7.71 (d, 2H), 7.23 (d, 2H), 7.08 (d, 1H), 6.75 (d, 1H), 4.74 (broad d, 1H), 3.42 (6-line m, 1H), 2.88 (d, 2H), 2.41 (s, 3H), 1.68–1.25 (m, 2H), 0.85 (t, 3H). $^{13}$C NMR (50 MHz, CDCl$_3$): δ 143.08, 137.69, 132.12, 129.56, 127.43, 126.96, 123.63, 123.34, 55.88, 32.66, 27.33. 21.50, 9.79. Analysis calculated for C$_{15}$H$_{18}$ClNO$_2$S$_2$: C, 52.39; H, 5.28; N, 4.10. Found: C. 52.25; H, 4.99; N. 3.87.

EXAMPLE 8

Preparation of (R)-N-[1-[3-chlorothien-2-yl)methyl]propyl]-N-(2-fluoro-3-nitropyrid-4-yl)-4-methylbenzenesulfonamide and (R)-N-[1-[3-chlorothien-2-yl)methyl]propyl]-N-(2-chloro-3nitropyrid-4-yl)-4-methylbenzenesulfonamide Method A

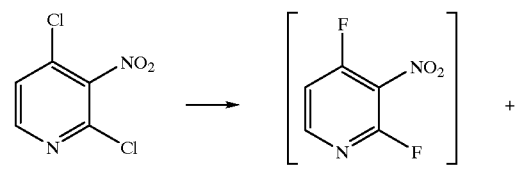

-continued

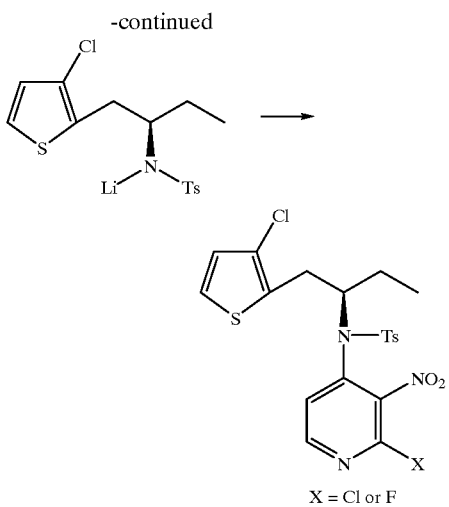

X = Cl or F (R)-N-[1-[3-chlorothien-1-yl)methyl]propyl]-N-(2-fluoro-3-nitropyrid-4-yl)-4-methylbenzenesulfonamide A mixture of 100 g (0.52 mol, 1 eq.) of 2,4-dichloro-3-nitropyridine, 105 g (1.81 mol, 3.48 eq.) of potassium fluoride and 11.73 g (0.036 mol, 0.07 eq.) of tetrabutylammonium bromide (TBAB) in 500 ml of toluene and 330 ml of 1-methyl-2-pyrrolidinone is heated with stirring in a first reaction vessel at 115–120 ° C. for 4.5 hours. The reaction mixture is cooled to 20° C. and filtered into a second reaction vessel using 170 ml of 1-methylpyrrolidinone to transfer the batch. 160 g (0.456 mol. 0.88 eq.) of (R)-N-[1-[(3-chlorothien-2-yl)methyl]propyl]-4-methylbenzenesulfonamide lithium salt is then added to the mixture at 35° C. The reaction mixture is stirred at 85° C. for 3.5 hours and then cooled to 20° C. The cooled mixture is partitioned between 500 ml of brine, 1.6 L tert-butylmethyl ether and 200 ml of toluene. The organic layer is washed with 1 L of water, dried over magnesium sulfate and concentrated under reduced pressure. The resulting solid is dissolved in 200 ml of ethyl acetate and triturated with 65 ml of heptane. The mixture is cooled at −6° C. for 48 hours and the resulting solid is isolated by filtration and washed with a cold (−8° C.) mixture of ethyl acetate/heptane (4:1 v/v). The solid is dried under vacuum with a nitrogen bleed at 40–45° C. to give (R)-N-[1-[3-chlorothien-2-yl )methyl] propyl]-N-(2-fluoro-3-nitropyrid-4-yl)-4-methylbenzenesulfonamide (138.7 g. 63% yield. 95.4 A% pure (HPLC)).

(R)-N-[1-[3-chlorothien-2-yl)methyl]propyl]-N-(2-fluoro-3-nitropyrid-4-yl)-4-methylbenzenesulfonamide and (R)-N-[1-[3-chlorothien-2-yl)methyl]propyl]-N-(2-chloro-3-nitropyrid-4-yl)-4-methylbenzenesulfonamide.

A mixture of 150.0 g (0.781 mol) of 2,4-dichloro-3-nitropyridine, 226.5.g (3.9 mol) of potassium fluoride (spray dried), 75.0 g (0.233 mol) tetrabutyl-ammonium bromide (TBAB) and 800 ml of toluene is heated to reflux with a Dean-Stark trap attached to the reaction vessel. Approximately 100 ml of toluene is distilled off after which the mixture is cooled to 60° C. and 254.7 g (0.741 mol) (R)-N-[1-[(3-chlorothien-2-yl)methyl]propyl]-4-methylbenzenesulfonamide lithium salt is added. The mixture is heated at reflux for 4 hours and then cooled to room temperature. 800 ml of water is added and the reaction mixture stirred for 10 minutes. The layers are separated. The organic layer is washed twice with 800 ml of water, insoluble material is removed by filtration and the filtrate is concentrated under reduced pressure. Crystallized solid is slurried with 1 L of methanol for 1 hour at room temperature. The methanol is removed by filtration and the solid is slurried with 1 L of heptane for 1 hour. The heptane is removed by filtration and the solid is slurried with 1 L of methanol for 1 hour. The product is air-dried on the filter, then dried under vacuum at room temperature with a nitrogen bleed for 16 hours to give (R)-N-[1-[3-chlorothien-2-yl)methyl]propyl]-N-(2-fluoro-3-nitropyrid-4-yl)-4-methylbenzenesulfonamide (225.7 g, 60% yield. 95 A% pure (HPLC). The product contains approximately 2 A% of (R)-N-[1-[3-chlorothien-2-yl)methyl]propyl]-N-(2-chloro-3-nitropyrid-4-yl)-4-methylbenzenesulfonamide.

Method B

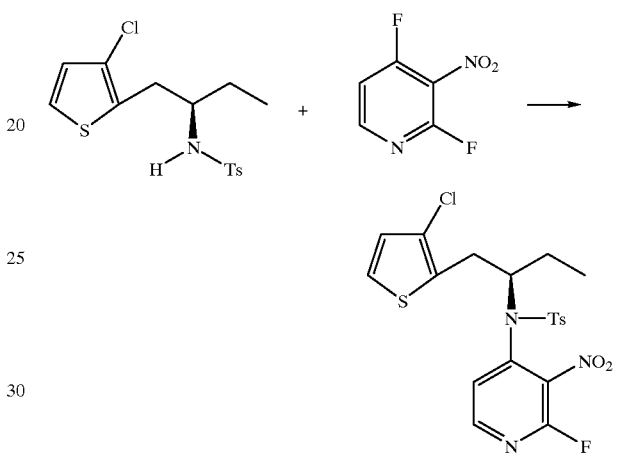

A first solution containing 43.55 g (0.127 mol) of (R)-N-[1-[(3-chlorothien-2-yl)methyl]propyl]-4-methylbenzenesulfonamide in 71 ml of tetrahydrofuran (THF) is prepared and cooled to 4° C. 138 ml (0.138 mol) of a 1.0 M solution of potassium tert-butoxide in tetrahydrofuran is added dropwise to the first solution. The resulting mixture is stirred for 15 minutes at 20° C. 23.7 g (0.149 mol) of 2,4-difluoro-3-nitropyridine in 10 ml of tetrahydrofuran is then added and the mixture heated at 65° C. for 1 hour. The mixture is cooled to room temperature and partitioned between 150 ml of water and 300 ml of ethyl acetate. The layers are separated. The organic layer is washed twice with 150 ml of water, once with 100 ml of brine, dried over anhydrous magnesium sulfate and concentrated under reduced pressure. The residue is slurried with 100 ml of methanol, then with 150 ml of heptane and then with 60 ml of methanol. The residue is vacuum dried at room temperature with a nitrogen bleed to afford (R)-N-[1-[3-chlorothien-2-yl)methyl]propyl]-N-(2-fluoro-3-nitropyrid-4-yl)-4-methylbenzenesulfonamide (51.1 g, 83.4% yield. 97.6 A% (HPLC)) as a white solid. MS (ion spray)(relative intensity) 484/486 (75), 312 (100).

A small sample of the crude product is recrystallized from THF/CH$_3$CN/H$_2$O. M$_p$.: 139° C. $^1$H NMR (200 MHz, CDCl$_3$): δ 8.30 (1H, d broad), 7.73 (2H, d broad), 7.38–7.15 (3H, m), 7.16 (1H, d), 6.82 (1H, d), 3.95 (1H, m), 3.27 (1H, dd), 3.02 (1H, dd), 2.45 (3H, s), 1.6 (2H, m broad), 0.70 (3H, t broad). $^{13}$C NMR (50 MHz. CDCl$_3$): δ 157.565, 152.696. 148.771, 148.445, 145.131, 132.348, 129.945, 128.224, 127.757, 125.370, 125.267, 123.966, 123.768, 67.078, 32.346, 26.081, 21.648. 11.617. Analysis calculated for C$_{20}$H$_{19}$ClFN$_3$O$_4$S$_2$: C, 49.64; H, 3.96; N, 8.68. Found: C, 49.68; H, 3.96; N, 8.76.

EXAMPLE 9

Preparation of [3aR-[3aα,4α,6a(R*),6aα]]-6-[7-[[1-[(3-chlorothien-2-yl)methyl]propyl][4-methylbenzenesulfonyl] amino]-3H-imidazo[4,5-b]pyrid-3-yl]N-ethyl tetrahydro-2, 2-dimethyl-4H-cyclopenta-1,3-dioxole-4-carboxamide.

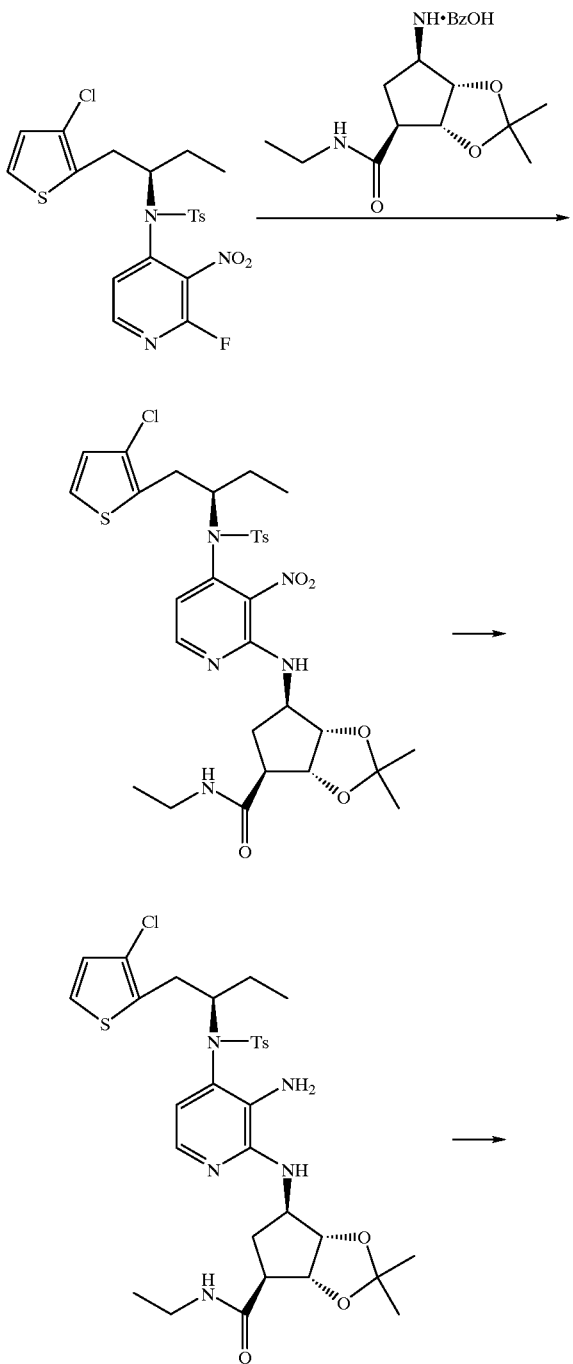

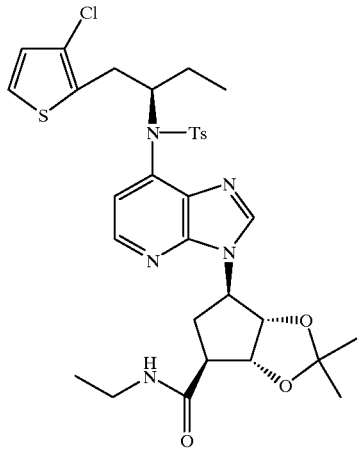

Method A

Step 1: [3aR-[3aα,4α,6α(R*),6aα]]-6-[4-[[1-[(3-chlorothien-2-yl)methyl]propyl][4-methylbenzenesulfonyl] amino]-3-nitropyrid-2-ylamino]N-ethyl tetrahydro-2,2-dimethyl-4H-cyclopenta-1,3-dioxole-4-carboxamide.

A mixture of 25.0 g (0.052 mol) (R)-N-[1-[3-chlorothien-2-yl)methyl]-propyl]-N-(2-flouro-3-nitropyrid-4-yl)-4-methylbenzenesulfonamide, 19.9 g (0.057 mol) 3aR-[3aα, 4α,6a,6aα]-6-amino-N-ethyltetrahydro-3,3-dimethyl-2,4-dioxabicyclo [3,3,0]octan-8-carboxamide, benzoate, 21.5 g (0.155 mol) of potassium carbonate (325 mesh) and 200 ml of ethyl acetate is heated at 80° C. with stirring for 1.5 hours. The mixture is cooled to 20° C. 100 ml of water is added and the layers are separated. The organic layer is washed with 100 ml of half saturated brine. HPLC shows the [3aR[3aα, 4α,6a(R*),6aα]]-6-[4-[[1-[(3-chlorothien-2-yl)methyl] propyl][4-methylbenzenesulfonyl]amino]-3-nitropyrid-2-ylamino]N-ethyl tetrahydro-2,2-dimethyl-4H-cyclopenta-1, 3-dioxole-4-carboxamide to be 94.9 A% pure. This ethyl acetate solution is used "as is" in the next step.

A small sample of the solution is concentrated under vacuum and then purified by flash chromatography ($SiO_2$, ethyl acetate/heptane 1:1) to give a bright yellow solid showing 98 A% purity by HPLC. HRMS (FAB) calculated for $C_{31}H_{38}ClN_5O_7S_2(M+H)^-$ 692.1979, found 692.1931. $^1H$ NMR (500 MHz, $CDCl_3$) (mixture of conformational isomers, ratio ca. 7:3, all signals reported): 8.33 (d), 8.25 (d, minor conformer), 7.94 (d), 7.87 (d), 7.76 (d), 7.34 (d), 7.30 (d), 7.13 (m), 6.81 (m), 6.56 (d), 6.47 (d, min. conf.), 5.66 (m), 4.81 (d, min. conf.), 4.74 (m), 4.58 (d, min. conf.), 4.56 (d), 3.99(m), 3.87 (m), 3.35 (m), 3.21 (dd, min. conf.), 3.10 (dd); 2.90 (dd), 2.82 (dd), 2.55 (m), 2.41 (s), 2.13 (d), 1.96 (d, min. conf.), 1.64 (m), 1.60 (s), 1.52 (s), 1.30 (s), 1.22 (s), 1.40–1.20 (m), 1.15 (t), 0.88 (t), 0.64 (t, min. conf.), 0.51 (t). $^{13}C$ NMR (50 MHz, $CDCl_3$) (mixture of conformational isomers, as above): 173.781, 151.181, 144.504, 139.049, 135.972, 133.204, 129.715, 128.772, 128.089, 127.654, 123.641, 123.411, 114.768, 110.787, 86.284, 84.833, 64.913, 57.380, 53.328, 34.788, 32.361, 31.085, 30.680, 26.692, 24.297, 21.632, 14.718, 11.395.

Step 2: [3aR-[3aα,4α,6aα]]-6-[4-[[1-[(3-chlorothien-2-yl) methyl]propyl][4-methylbenzenesulfonyl]amino]-3- aminopyrid-2-ylamino] N-ethyl tetrahydro-2,2-dimethyl-4H-cyclopenta-1,3-dioxole-4-carboxamide.

The ethyl acetate solution of [3aR-[3aα,4α,6aα]]-6-[4-[[1-[(3-chlorothien-2-yl)methyl]propyl][4-methylbenzenesulfonyl]amino]-3-nitropyrid-2-ylamino] N-ethyl tetrahydro-2,2-dimethyl-4H-cyclopenta-1,3-dioxole-4-carboxamide from the previous step is diluted with 220 ml of methanol. The solution is then hydrogenated in the presence of platinum on carbon (3.5 g, Degussa type F101 RA/W, 5% Pt. 50% water) under 50–55 psi of hydrogen for 24 hours at room temperature. The mixture is filtered through a glass microfiber filter and the filter cake washed with 100 ml of hot ethyl acetate. The combined filtrates are concentrated under vacuum to give the title compound (90 A% (HPLC)) as an oil.

A small sample of the oil is triturated with $Et_2O$ to give the title compound as an off-white solid. $M_p$: 175–177° C. HRMS (FAB) calculated for $C_{31}H_{41}ClN_5O_5S_2$ $(M+H)^-$ 662.2237, found 662.222. $^1H$ NMR (200 MHz, $CDCl_3$) (mixture of conformational isomers. ratio ca. 7:3, all signals reported): δ 7.75 (d), 7.63 (d), 7.54 (d), 7.27 (d), 7.21 (s), 7.15 (dd), 6.82 (dd), 6.64 (d), 6.48 (d, minor conformer), 5.95 (d, min. conf.), 5.83 (d), 5.80(br.m), 4.78 (m), 4.60 (m), 4.39, (m), 3.99 (s), 3.75 (s, min. conf.), 3.27 (dt), 3.12 (dd, min. conf.), 2.90–2.45 (m), 2.42 (s), 2.41 (1s, min. conf), 2.04 (apparent t), 1.81 (s), 1.48 (s), 1.47 (s, min. conf.), 1.55–1.22 (m), 1.30 (s), 1.29 (s. min. conf.), 1.16 (t), 1.15(t, min. conf.), 1.04 (t), 0.73 (t). $^{13}C$ NMR (50 MHz, $CDCl_3$) (mixture of conformational isomers, all signals reported): δ 174.97, 174.84, 149.88, 149.53, 143.77, 143.60, 137.42, 136.47, 136.32, 133.45, 131.55, 131.08, 129.66, 129.38, 127.94, 127.73, 127.59, 125.99, 125.88, 123.59, 123.23, 123.10, 114.47, 114.05, 110.71, 86.36, 85.94, 85.13, 84.72, 64.46, 64.20, 56.90, 56.75, 53.99, 53.74, 34.92, 34.83, 32.58, 32.13, 31.23. 26.84, 26.78, 26.05, 24.96, 24.44, 21.59, 14.70, 12.57, 12.08.

Step 3: [3aR-[3aα,4α,6a(R*),6aα]]-6-[7-[[1-[(3-chlorothien-2-yl)methyl]propyl][4-methylbenzenesulfonyl]amino]-3H-imidazo[4,5-b]pyrid-3-yl]N-ethyl tetrahydro-2,2-dimethyl-4H-cyclopenta-1,3-dioxole-4-carboxamide.

A mixture of ≦0.052 mol of the crude [3aR-[3aα,4α,6aα]]-6-[4-[[1-[(3-chlorothien-2-yl)methyl]propyl][4-methylbenzenesulfonyl]amino]-3-aminopyrid-2-ylamino] N-ethyl tetrahydro-2,2-dimethyl-4H-cyclopenta-1,3-dioxole-4-carboxamide from the previous step, 74.0 g (0.50 mol) of triethylorthoformate and 100 ml (108.2 g, 1.06 mol) of acetic anilydride is heated at 100–105° C. for 2 hours. The mixture is cooled to room temperature. The cooled reaction mixture is diluted with 168 ml of 2-propanol and stirred for 1 hour, resulting in the formation of a solid suspension. The mixture is cooled to 4° C. and the solid is isolated by filtration. An additional crop of product is obtained by adding heptane to the mother liquor and isolating the solid by filtration. The combined filter cakes are washed with 90 ml of cold 2-propanol, air dried, and then dried under vacuum with a nitrogen bleed for two days to give the title compound (25.57 g, 95.82 A% (HPLC)) as a white powder. The yield is 73% overall for the three steps from (R)-N-[1-[3-chlorothien-2-yl )methyl]propyl]-N-(2-fluoro-3-nitropyrid-4-yl)-4-methylbenzenesulfonamide and 61% from 2,4-difluoro-3-nitropyridine. MS (ion spray): 672/674 (100). $^1H$ NMR (200 MHz, $CDCl_3$): δ 8.38 (1H, d), 8.15 (1H, s), 7.85 (1H, d), 7.25 (1H, s), 7.22 (1H, d), 7.15 (2H, dd), 6.78 (1H, d), 5.85 (1H, t), 5.05 (3H, m), 4.25 (1H, m), 3.28 (3H, m), 2.85 (3H, m), 2.60 (1H, q), 2.40 (3H, s), 1.60 (3H, s), 1.45 (2H, q), 1.25 (3H, s), 1.20 (3H, t), 0.90 (3H, t). $^{13}C$ NMR (500 MHz $CDCl_3$): δ 171.36 149.04, 144.51, 143.53, 142.90, 137.70, 136.37, 135.34, 133.86, 129.45, 128.11, 127.46, 123.39, 123.21, 121.08, 114.22, 83.86, 81.88, 64.99, 60.69, 50.24, 34.63, 34.38, 33.35, 27.45, 25.26, 25.07, 21.58, 14.81, 11.64.

A sample of the crude material is recrystallized from ethyl acetate/$CH_3CN$. $M_p$: 197–199° C. The structure of [3aR-[3aα,4α,6a(R*),6aα]]-6-[7-[[1-[(3-chlorothien-2-yl)methyl]propyl][4-methylbenzenesulfonyl]amino]-3H-imidazo[4,5-b]pyrid-3-yl] N-ethyl tetrahydro-2,2-dimethyl-4H-cyclopenta-1,3-dioxole-4-carboxamide including the absolute configuration, is confirmed by single crystal X-ray analysis.

Method B

Step 1: [3aR-[3aα,4α,6a(R*),6aα]]-6-[4-[[1-[(3-chlorothien-2-yl)methyl]propyl][4-methylbenzenesulfonyl]amino]-3-nitropyrid-2-ylamino] N-ethyl tetrahydro-2,2-dimethyl- 4H-cyclopenta-1,3-dioxole-4-carboxamide A mixture of 123.0 g (0.254 mol) of (R)-N-[1-[3-chlorothien-2-yl)methyl]propyl]-N-(2-fluoro-3-nitropyrid-4-yl)-4-methylbenzenesulfonamide, 97.8 g (0.279 mol) of 3aR-[3aα,4α,6a,6aα]-6-amino-N-ethyltetrahydro-3,3-dimethyl-2,4-dioxabicyclo [3.3.0]octan-8-carboxamide benzoate, 105.3 g (0.762 mol) potassium carbonate (325 mesh) and 1 L of 1-methyl-2-pyrrolidinone is heated at 85° C. with stirring for 1.5 hours. The reaction mixture is cooled to room temperature and poured into 2.5 L of water with stirring. A solid is isolated by filtration and the filter cake is washed with 10 L water. The filter cake is air-dried on the filter overnight and then dried under vacuum with a nitrogen bleed for 4 days to provide the title compound (179 g, 98 A% (HPLC)) as a yellow solid.

It should be noted that 1-methyl-2-pyrrolidinone (NMP) may be replaced with ethyl acetate (EtOAc). The solvent volume, temperature and reaction time (80° C.) are nearly identical. The work up involves a water wash to remove remaining 3aR-[3aα,4α,6a,6aα]-6-amino-N-ethyltetrahydro-3,3-dimethyl-2,4-dioxabicyclo [3.3.0] octan-8-carboxamide benzoate. The NMP solvent accelerates the reactivity of the chloro compound, i.e., (R)-N-[1-[3-chlorothien-2-yl)methyl]propyl]-N-(2-chloro-3-nitropyrid-4-yl)-4-methylbenzenesulfonamide which reacts very slowly in ethyl acetate.

Step 2: [3aR-[3aα,4α,6a(R*),6aα]]-6-[4-[[1-[(3-chlorothien-2-yl)methyl]propyl][4-methylbenzenesulfonyl]amino]-3-aminopyrid-2-ylamino] N-ethyl tetrahydro-2,2-dimethyl-4H-cyclopenta-1,3-dioxole-4-carboxamide.

A solution of [3aR-[3aα,4α,6a(R*),6aα]]-6-[4-[[1-[(3-chlorothien-2-yl)methyl]propyl][4-methylbenzenesulfonyl]amino]-3-nitropyrid-2-ylamino] N-ethyl tetrahydro-2,2-dimethyl-4H-cyclopenta-1,3-dioxole-4-carboxamide (90.0 g. 0.13 mol) in 1.1 L of ethyl acetate is washed three times with 500 ml water. The solution is then diluted with 300 ml of methanol and hydrogenated in the presence of platinum on carbon (8.8 g, Degussa type F101 RA/W, 5% Pt. 50% water) under 50–55 psi of hydrogen for 24 hours room temperature. The reaction mixture is filtered through a glass microfiber filter and the filter is washed with 300 ml of hot ethyl acetate. The combined filtrates are evaporated under reduced pressure to give a solid which is then slurried with 800 ml of heptane and isolated by filtration. The filtercake is dried under vacuum with a nitrogen bleed for 2 days to provide the title compound (94.5 g, 89 A% (HPLC)).

Step 3: [3aR-[3aα,4α,6a(R*),6aα]]-6-[7-[[1-[(3-chlorothien-2-yl)methyl]propyl][4-methylbenzenesulfonyl]amino]-3H-imidazo[4,5-b]pyrid-3-yl]N-ethyl tetrahydro-2,2-dimethyl-4H-cyclopenta-1,3-dioxole-4-carboxamide.

A mixture of 94.5 g (0.13 mol) of [3aR-[3aα,4α,6a(R*),6aα]]-6-[4-[[1-[3-chlorothien-2-yl)methyl]propyl][4-methylbenzenesulfonyl]amino]-3-nitropyrid-2-ylamino]N-ethyl tetrahydro-2,2-dimethyl-4H-cyclopenta-1,3-dioxole-4-carboxamide from the previous step, 141.0 ml (0.85 mol) of triethylorthoformate and 114.0 ml (1.21 mol) of acetic anhydride is heated at 100–105° C. for 2 hours. The reaction mixture is cooled to room temperature. The cooled reaction mixture is diluted with 1 L of heptane and stirred for 1 hour. The solids formed are isolated by filtration. washed with 500 ml of cold heptane and dried under vacuum with a nitrogen. bleed for two days to provide the title compound (65.0 g 75% yield, 97.0 A% (1HPLC)).

EXAMPLE 10

Preparation of [3aR-[3aα,4α,6a(R*),6aα]]-6-[7-[[1-[(3-chlorothien-2-yl)methyl]propyl]amino]-3H-imidazo[4,5-b]pyrid-3-yl]N-ethyl tetrahydro-2,2-dimethyl-4H-cyclopenta-1,3-dioxole-4-carboxamide.

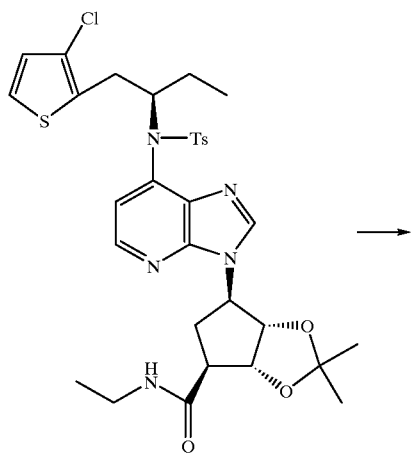

Method A

1–2 small crystals of iodine are added to a mechanically stirred suspension of 3.9 g (0.16 mol) of magnesium turnings in 30 ml of methanol under nitrogen. Bubbles are observed rising from the magnesium as the mixture starts warming up. A solution containing 20 g (0.03 mol) of [3aR-[3aα,4α,6a(R*),6aα]]-6-[7-[[1-[(3-chlorothien-2-yl)methyl]propyl][4-methylbenzenesulfonyl]amino]-3H-imidazo[4,5-b]pyrid-3-yl] N-ethyl tetrahydro-2,2-dimethyl-1H-cyclopenta-1,3-dioxole-4-carboxamide in a mixture of 65 ml of methanol and 55 ml of toluene is added over 20 minutes, while maintaining the reaction temperature at about 40° C. The mixture is stirred at about 40° C. for approximately 3 hours. The mixture is then cooled to room temperature, concentrated to ½ of the original volume and filtered through ca. 50 g celite. The filter is washed with 150 ml of ethyl acetate and the combined filtrate is washed with 150 ml of water and 150 ml of brine. The organic phase is dried with magnesium sulfate and concentrated under reduced pressure to provide the title compound (15.4 g, 85 A%, (HPLC)).

Method B

A solution of lithium triethylborohydride (1.0 N in THF, 18.6 ml, 1.86 mmol, 2.5 eq.) is added dropwise to a magnetically stirred solution containing 5.0 g (7.43 mmol) of [3aR-[3aα,4α,6a(R*),6aα]]-6-7-[[1-[(3-chlorothien-2-yl)methyl]propyl][4-methylbenzenesulfonyl]amino]-3H-imidazo[4,5-b]pyrid-3-yl]N-ethyl tetrahydron-2,2-dimethyl-4H-cyclopenta-1,3-dioxole-4-carboxamide in 66 ml off THF at about 4° C. under nitrogen. Following the end of the addition, the mixture is stirred at room temperature for 2 hours. HPLC showed ≦3 A% of starting material and ca. 90 A% of [3aR-[3aα,4α,6a(R*),6aα]]-6-[7-[[1-[(3-chlorothien-2-yl)methyl]propyl]amino]-3H-imidazo[4,5-b]pyrid-3-yl]N-ethyl tetrahydro-2,2-dimethyl-4-H-cyclopenta-1,3-dioxole-4-carboxamide.

30 ml of water and 20 ml of ethyl acetate are added and the phases are separated. The organic phase is washed with water and with brine, dried over magnesium sulfate and concentrated under reduced pressure to provide the title compound (3.7 g, 85A% (HPLC)) as a light yellow solid.

EXAMPLE 11

Preparation of [1S-[1α,2β,3β,4α(S*)]]-4-[7-[[1-[(3-chlorothien-2-yl)methyl]propyl]amino]-3H-imidazo[4,5-b]pyrid-3-yl]N-ethyl 2,3-dihydroxycyclopentanecarboxamide.

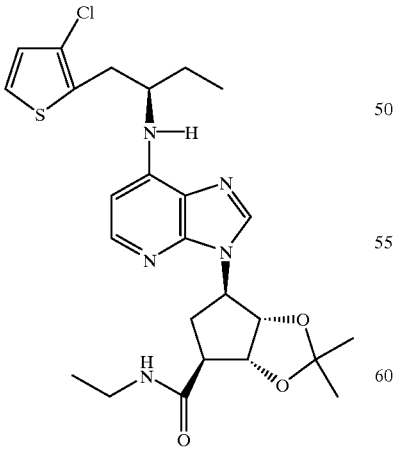

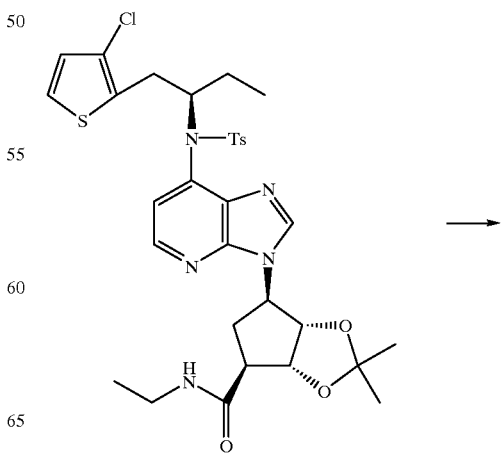

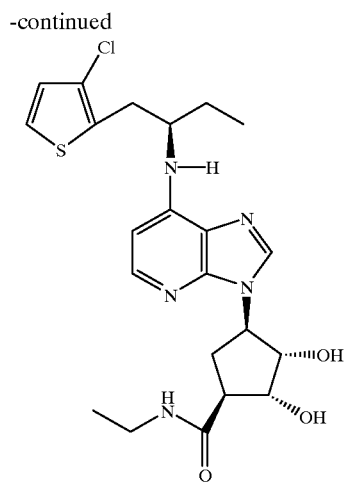

Method A

A mixture of 5.0 g((0.0074 mol) of [3aR-[3aα,4α,6a(R*), 6aα]]-6-[7-[[1-[(3-chlorothien-1-yl)methyl]propyl][4-methylbenzenesulfonyl]amino]-3H-imidazo[4,5-b]pyrid-3-yl]N-ethyl tetrahedro-2,2-dimethyl-4H-cyclopenta-1,3-dioxole-4-carboxamide, 8.88 g (6.0 ml, 0.0778 mol, 10.5 eq.) of triluoroacitic acid (TFA) and 4.42 g (3.6 ml, 0.0186 mol, 2.51 eq.) of trimethylsilyl trifluoromethanesulfonate in 15 ml of toluene is heated with stirring at 70° C. for 2 hours. The mixture is cooled to 20° C. and 50 ml of toluene is added, followed by 50 ml of concentrated hydrochloric acid. The mixture is stirred for 45 minutes and then the layers are separated. The aqueous layer is extracted with 20 ml of tetrahydrofuran and then with 65 ml of toluene. The combined organic layers are discarded.

50 ml of n-butyl acetate (n-BuOAc) is added to the aqueous layer. The mixture is cooled to ca. 4° C. and basified with ca. 37 g of sodium carbonate. The layers are separated and the aqueous layer is extracted twice with 50 ml of n-butyl acetate. The organic layers are combined and washed twice with 50 ml of water. The organic layer is concentrated to approximately 40% of the original volume and seeded with [1S-[1α,2β,3β,4α(S*)]]-4-[7-[[1-[(3-chlorothien-2-yl)methyl]propyl]amino]-3H-imidazo[4,5-b]pyrid-3-yl]N-ethyl 2,3-dihydroxycyclopentanecarboxamide. The mixture is cooled to ca. 4° C. and is maintained at this temperature until the crystallization is complete. The solid is isolated by filtration and dried under vacuum with a nitrogen bleed to constant weight to provide the title compound (2.51 g, 70% yield) as the hemi-hydrate. Analysis calculated for $C_{22}H_{28}ClN_5O_3S \times 0.5(H_2O)$: C, 54.26; H, 6.00; N, 14.38; Cl, 7.28. Found: C, 54.06; H, 5.94; N, 14.38; Cl, 7.28. MS (ion spray) 478/480 ((M+H), 100), 346 (55). $^1$H NMR (200 MHz, DMSO-D6): δ 8.23 (1H, s), 8.06 (1H, t), 7.84 (1H, d), 7.42 (1H, d), 6.96 (1H, d), 6.63 (1H, broad d), 6.34 (1H, d), 5.16 (1H, broad d), 4.94(1H, d),4.76 (1H, q), 4.33(1H, m), 4.11 (1H, q), 3.12 (2H, q),3.07 (2H, m) 2.73 (1H, m), 2.51 (1H, m), 2.39 (1H, dt), 2.09 (1H, dt), 1.63 (2H, m), 1.05 (3H, t), 0.92 (3H, t). $^{13}$C NMR (50 MHz, DMSO-D6): δ 172.73 (C), 147.42 (C), 146.12 (C), 144.37 (CH), 138.74 (CH), 134.079 (C), 126.671 (Cl), 124.516 (C), 122.779 (C), 121.626 (CH), 96.938 (CH), 75.073 (CH), 73.07 (CH), 58.61 (CH), 54.20 (CH), 48.81 (CH), 33.45 (CH$_2$), 32.19 (CH$_2$) 30.06 (CH$_2$), 27.23 (CH$_2$), 14.66 (CH$_3$), 10.40 (CH$_3$).

Method B 0.0146 mol of methanesulfonic acid is added to a mechanically stirred mixture of 0.0074 mol of [3aR-[3aα, 4α,6a(R*),6aα]]-6-[7-[[1-[(3-chlorothien-2-yl)methyl]propyl][4-methylbenzenesulfonyl]amino]-3H-imidazo[4,5-b]pyrid-3-yl]N-ethyl tetrahydro-2,2-dimethyl-4H-cyclopenta-1,3-dioxole-4-carboxamide in 10 ml oftritluoroacetic acid (TFA) and 0.0146 mol thioanisole under nitrogen. The reaction mixture is heated at 85° C. for 3 hours. The solvents are removed in vacuo. 25 ml of toluene is added and removed under reduced pressure (azeotrope). The resulting tan-colored oily solid is partitioned between ethyl acetate and 175 ml of cold 1N aqueous NaOH. The aqueous phase is extracted with 100 ml of ethyl acetate and the combined organic extracts are washed with 100 ml of brine. dried over magnesium sulfate and concentrated under reduced pressure to provide 3.4 g of a tan-colored solid.

The crude material is dissolved in 25 ml of ethyl acetate. The solution is stirred and 2.0 ml of concentrated HCl is added dropwise over 1 minute. A gummy solid precipitates and solidifies within 5 minutes. 25 ml of ethyl acetate is added and the suspension is stirred at room temperature overnight. A resulting off-white solid is isolated by filtration, washed with 20 ml of cold ethyl acetate and dried under reduced pressure at 40–50° C. to give the title compound (2.4 g, 58% yield) as the bis HCl salt. The free base can be liberated using the second part of the "Hydrolysis" procedure below.

Alternatively, a mixture of 1 eq of [3aR-[3aa,4a,6a(R*), 6aa]]-6-[7-[[1-[(3-chlorothien-2-yl)methyl]propyl][4-methylbenzenesulfonyl]aminio]-3H-imidazo]4,5-b]pyrid-3-yl]N-ethyl tetrahydro-2,2-dimethyl-4H-cyclopenta-1,3-dioxole-4-carboxamide, 2.1 eq of methane sulfonic acid and 2eq of water in trifluoroacetic acid is heated at 60° C. The reaction mixture is then washed with heptane (4x), made basic with Na$_2$CO$_3$/ethyl acetate/H$_2$O and concentrated in vacuo. The residue is taken tip in n-butyl acetate and the title compound (73% yield, 96% pure (HPLC)) is crystallized by addition of methyl tert-butyl ether. This material is further purified by recrystallization from n-butyl acetate (with 2 eq water) to give the title compound (97% pure (HPLC)).

EXAMPLE 12

Preparation of [1S-[1α,2β,3β,4α(S*)]]-4-[7-[[1-[(3-chlorothlien-2-yl)methyl]propyl]amino]-3H-imidazo[4,5-b]pyrid-3-yl]N-ethyl 2,3-dihydroxycyclopentanecarboxamide.

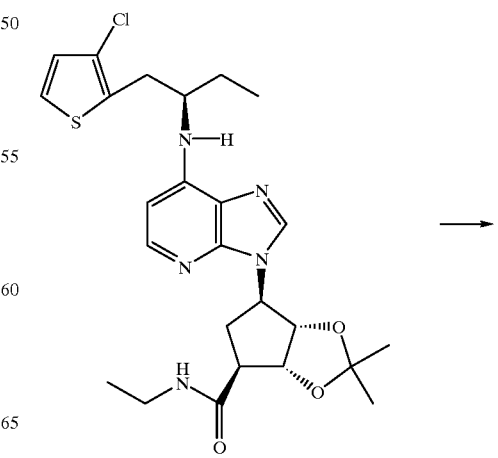

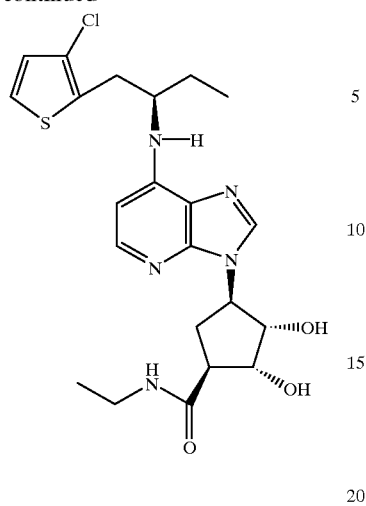

9.4 ml of concentrated (37%) HCl is added to a magnetically stirred mixture of 14.2 g (ca. 0.027 mol) of crude [3aR-[3aα,4α,6a(R*),6aα]]6-[7-[[1-[(3-chlorothien-2-yl)metihyl]propyl]amino]-3H-imidazo[4,5-b]pyrid-3-yl]N-ethyl tetrahydro-2,2-dimethyl-4H-cyclopenta-1,3-dioxole-4-carboxamide in 32 ml of tetrahydrofuran over 10 minutes while maintaining the mixture temperature below 35° C. Following the end of the addition, the mixture is stirred for 3 hours at room temperature, after which a precipitated solid is isolated by filtration. The solid is washed with cold (5–10° C.) ethyl acetate and dried to constant weight to give the title compound (8.0 g) as its bis HCl salt.

The HCl salt is partitioned between 100 ml of n-butyl acetate and 50 ml of a saturated aqueous sodium carbonate solution. The organic phase is washed with water and brine, cooled to room temperature and stirred for 16 hours. The reaction mixture is filtered and the solid is dried at 40–50° C. under reduced pressure to give the title compound (10 g, 75% yield).

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and articles cited herein are hereby incorporated herein by reference in their entirety and relied upon.

What is claimed is:
1. A process for preparing an N-protected N6-substituted adenosine isostere of formula

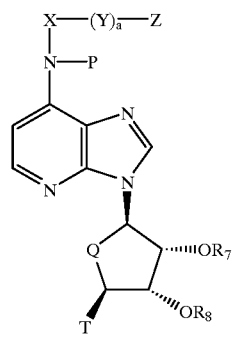

wherein
P is a nitrogen protecting group;
Q is $CH_2$;
T is

or $R_3O$—$CH_2$;
X is a straight or branched chain alkylene, cycloalkylene or cycloalkenylene group;
Y is $NR_4$, O or S;
a=0 or 1;
Z is of the formula

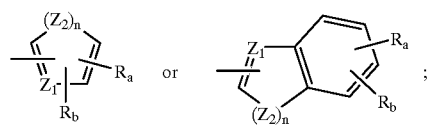

$Z_1$ is N, $CR_5$, $(CH)_m$—$CR_5$ or $(CH)_m$—N, m being 1 or 2;
$Z_2$ is N, $NR_6$, O or S;
n is 0 or 1;
$R_1$, $R_2$, $R_3$, $R_4$, $R_5$ and $R_6$ are independently H, alkyl, aryl or heterocyclyl;
$R_7$ and $R_8$ are independently H, alkyl, aralkyl, carbamoyl, alkyl carbamoyl, dialkylcarbamoyl, acyl, alkoxycarbonyl, aralkoxycarbonyl, aryloxycarbonyl, or $R_7$ and $R_8$ together may form

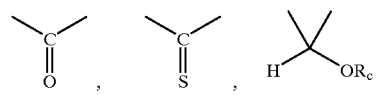

where $R_c$ is hydrogen or alkyl,

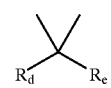

where $R_d$ and $R_e$ are independently hydrogen, alkyl, or $R_d$ and $R_e$ together with the carbon atom to which they are attached may form a cycloalkyl group; and $R_a$ and $R_b$ are independently H, OH, alkyl, hydroxyalkyl, alkyl mercaptyl, thioalkyl, alkoxy, alkyoxyalkyl, amino, alkyl amino, carboxyl, acyl, halogen, carbamoyl, alkyl carbamoyl, aryl or heterocyclyl, said process comprising reacting a 4-N-protected-2,3,4-triaminopyridine compound of formula

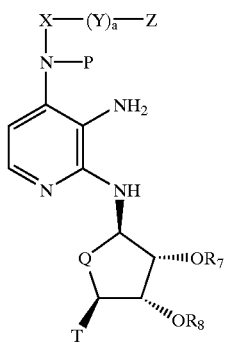

with a formic acid derivative, where heterocyclyl is about a 4 to about a 10 membered ring structure in which one or more of the atoms in the ring is N, O or S, and which may be aromatic or non-aromatic.

2. The process of claim 1 wherein P is selected from the group consisting of methanesulfonyl, trifluoromethanesulfonyl, benzenesulfonyl, p-toluenesulfonyl, p-methoxybenzenesulfonyl, phenacylsulfonyl, methoxycarbonyl, ethoxycarbonyl, 2,2,2-trichloroethoxycarbonyl, 2-trimethylsilylethyloxycarbonyl, tert-butoxycarbonyl, formyl, acetyl, benzoyl, trifluoroacetyl, benzyl and diphenylphosphinoyl.

3. The process of claim 1 wherein P is selected from the group consisting of methanesulfonyl, trifluoromethanesulfonyl, benzenesulfonyl, p-toluenesulfonyl, p-methoxybenzenesulfonyl and phenacylsulfonyl.

4. The process of claim 3 wherein

Q is $CH_2$;

T is

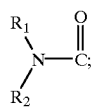

X is a straight or branched chain alkylene;
a=0,
Z is

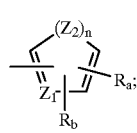

$Z_1$ is N, $CR_5$, $(CH)_m$—$CR_5$ or $(CH)_m$—N, m being 1 or 2;
$Z_2$ is N, $NR_6$, O or S;
n is 0 or 1;
$R_1$, $R_2$, $R_5$ and $R_6$ are independently H or alkyl;

$R_7$ and $R_8$ are alkyl, or $R_7$ and $R_8$ together may form

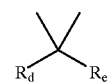

where $R_d$ and $R_e$ are independently hydrogen or alkyl, or together with the carbon atom to which they are attached may form a 1,1-cycloalkyl group; and $R_a$ and $R_b$ are independently H, OH, alkyl, hydroxyalkyl, alkyl mercaptyl, thioalkyl, alkoxy, alkyoxyalkyl, amino, alkyl amino, carboxyl, acyl, halogen, carbamoyl, alkyl carbamoyl, aryl or heterocyclyl.

5. The process of claim 1 further comprising removing the nitrogen protecting group P.

6. The process of claim 1 further comprising reducing a 4-N-protected 3-nitro-2,4-diaminopyridine compound of formula

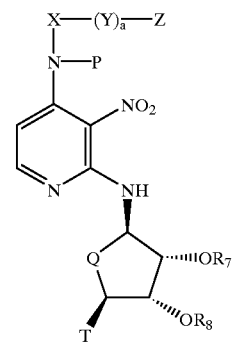

to form the 4N-protected-2,3,4-triaminopyridine compound of formula

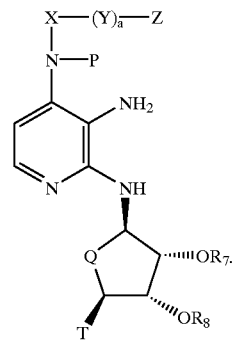

7. The process of claim 6 further comprising reacting an N-protected amino compound of formula P—NH—X—(Y)$_a$—Z with a 2,4-dihalo-3-nitropyridine compound of formula

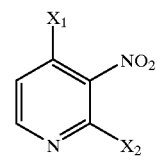

wherein $X_1$ and $X_2$ are independently Cl or F to form a 2-halo-3-nitro-4-N-protected aminopyridine compound of formula

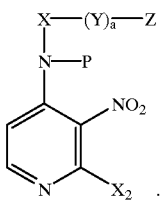

8. The process of claim 1 wherein the 4-N-protected 2,3,4-triaminopyridine compound is [3aR-[3aα,4α,6a(R*), 6aα]]-6-[4-[[1-[(3-chlorothiein-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide.

9. The process of claim 6 wherein the 4-N-protected 3-nitro-2,4-diaminopyridine compound is [3aR-(3aα, 4α,6a(R*),6aα]]-6-[4[[1-[(3-chlorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide.

10. The process of claim 7 wherein the N-protected amino compound of formula —NH—X—(Y)$_a$—Z is (R)-N-[1-[(3-chlorothien-2-yl)methyl]propyl]-4-methylbenzenesulfonamide or (R)—N-[1-[(3-chlorothien-2-yl)methyl]propyl]-4-methylbenzenesulfonamide lithium salt.

11. A process according to claim 1 for preparing [3aR-[3aα,4α,6a (R*),6aα]]-6-[7-[[1-[(3-chlorothien-2-yl)methyl]propyl][4-methylbenzenesulfonyl]amino-3H-imidazo[4,5-b]pyrid-3-yl]N-ethyl tetrahydro-2,2-dimethyl-4H-cyclopenta-1,3-dioxole-4-carboxamide comprising (i) reacting (R)-N-[1-[3-chlorothien-2-yl)methyl]propyl]-N-(2-fluoro-3-nitropyrid-4-yl)-4-methylbenzenesulfonamide with 3aR-[3aα,4α, 6a,6aα]-6-amino-N-ethyltetrahydro-3,3 -dimethyl-2,4-dioxabicyclo [3,3,0]octan-8-carboxamide, benzoate to form [3aR-[3aα,4a,6a(R*),6aα]]-6-[4-[[1-[(3-chlorothien-2-yl)methyl]propyl][4-methylbenzenesulfonyl]amino]-3-nitropyrid-2-ylamino]N-ethyl tetrahydron-2,2-dimethyl-4H-cyclopenta-1,3-dioxole-4-carboxamide, (ii) reducing the [3aR-[3aα, 4α,6a(R*),6aα]]-6-[4-[[1-[(3-chlorothien-2-yl)methyl]propyl][4-methylbenzenesulfonyl]aminio-3-nitropyrid-2-ylamino]N-ethyl tetrahydro-2,2-diminethyl-4H-cyclopenta-1,3-dioxole-4-carboxamide prepared in step (i) to form [3aR-[3aα4α,6a(R*),6aα]]-6-[[1-[3-clorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide and (iii) reacting the [3aR-[3aα,4α,6a(R*),6aα]]-6-[4-[[1-[(3-chlorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide prepared in step 2 above with an orthoformate ester, formamidine acetate or dimethylformamide dimethyl acetal, wherein steps (i)–(iii) are performed in a concatenated fashion without purification of the intermediate compounds [3aR-[3aα,4α,6a(R*),6aα]]-6-[4-[[1-[(3-chlorothien-2-yl)methyl]propyl][4-methylbenzenesulfonyl]amino]-3-nitropyrid-2-ylamino]N-ethyl tetrahydro-2,2-dimethyl-1-4H-cyclopenta-1,3-dioxole-4-carboxamide and [3aR-[3aα, 4α,6a(R*),6aα]]-6-[4-[[1-[(3-chlorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide.

12. A process for preparing (R)-N-[1-[3-chlorothien-2-yl)methyl]propyl]-N-(2-fluoro-3-nitropyrid-4-yl)-4-methylbenzenesulfonamide comprising (i) reacting 2,4-dichloro-3-nitropyridine with a fluorinating agent to form 2,4-difluoro-3-nitropyridine and (ii) reacting the product of step (i) with (R)-N-[1-[(3-chlorothien-2-yl )methylpropyl]-4-methylbenzensulfonamide lithium salt or (R)-N-[1-[(3-clorothien-2-yl)methyl]propyl]-4-methylbenzenesulfonamide, wherein steps (i) and (ii) are performed in a concatenated fashion without isolation of the product of step (i).

13. A process according to claim 1 for preparing [3aR-[3aα,4α, 6a(R*),6aα]]-6-[7-[[1-[3-chlorothien-2-yl)methyl]propyl][4-methylbenzenesulfonyl]amino]-3H-imidazo[4,5-b]pyrid-3-yl]N-ethyl tetrahydro-2,2-dimethyl-4H-cyclopenta-1,3-dioxole-4-carboxamide comprising (i) reacting 2,4-dichloro-3-nitropyridine with a fluorinating agent to form 2,4-difluoro-3-nitropyridine, (ii) reacting the 2,4-difluoro-3-nitropyridine with (R)-N-[1-[(3-chlorothien-2-yl)methyl]propyl]-4-methylbenzenesulfonamide lithium salt or (R)-N-[1-[(3-chlorothien-2-yl)methyl]propyl]-4-methylbenzenesulfonamide to form (R)-N-[1-[3-chlorothien-2-yl)methyl]propyl]-N-(2-fluoro-3-nitropyrid-4-yl)-4-methylbenzenesulfonamide, (iii) reacting the (R)-N-[1-[3-chlorothien-2-yl)methyl]propyl]-N-(2-fluoro-3-nitropyrid-4-yl)-4-methylbenzenesulfonamide with 3aR-[3aα,4α,6a, 6aα]-6-amino-N-ethyltetrahydro-3,3-dimethyl-2,4-dioxabicyclo[3,3,0]octan-8-carboxamide, benzoate to form [3aR-[3aα,4a,6a(R*),6aα]]-6-[4-[[1-[(3-chlorothien-2-yl)methyl]propyl][4-methylbenzenesulfonyl]amino]-3-nitropyrid-2-ylamino]N-ethyl tetrahydro-2,2-dimethyl-4H-cyclopenta-1,3-dioxole-4-carboxamide, (iv) reducing the [3aR-[3aα,4α,6a(R*),6aα]]-6-[-4-[[1-[(3-chlorothien-2-yl)methyl]benzenesulfonyl]amino]-3-nitropyrid-2-ylamino]N-ethyl tetrahydro-2,2-dimethyl-4H-cyclopenta-1,3-dioxole-4-carboxamide prepared in step (iii) to form [3aR-[3aα,4α,6a(R*), 6aα]]-6-[4-[[1-[(3-chlorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide and (v) reacting the [3aR-[3aα,4α,6a(R*),6a α]]-6-[4-[[1-[(3-chlorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide with an orthoformate ester, formamidine acetate or dimethylformamide dimethyl acetal, wherein steps (i)–(v) are performed in a concatenated fashion without purification of the intermediate compounds 2,4-dilfuoro-3-nitropyridine, (R)-N-[1-[3-chlorothien-2-yl)methyl]propyl]-N-(2-halo-3nitropyrid-4-yl)-4-methylbenzenesulfonamide, [3aR-[3aα,4α,6a(R*), 6aα]]-6-[4-[[1-[(3-chlorothien-2-yl)methyl]propyl][4-methylbenlzenesulfonyl]amino]-3-nitropyrid-2-ylamino]N-ethyl tetrahydro-2,2-dimethyl-4H-cyclopenta-1,3-dioxole-4-carboxamide and [3aR-[3aα, 4α,6a(R*),6aα]]-6-[4-[[1-[(3-chlorothien-2-yl)methyl]propyl][4-methylbenzenesulfonyl]amino]-3- aminopyrid-2-ylamino]N-ethyl tetrahydro-2,2-dimethyl-4H-cyclopeta-1,3-dioxole-4-carboxamide.

14. A compound of formula

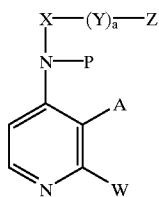

wherein

A is NH$_2$ or NO$_2$;

P is a nitrogen protecting group;

W is Cl, F or a group of formula

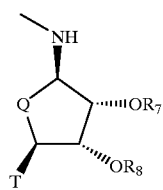

Q is CH$_2$;

T is

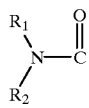

or R$_3$O—CH$_2$;

X is a straight or branched chain alkylene, cycloalkylene or cycloalkenylene group;

Y is NR$_4$, O or S;

a=0 or 1;

Z is of the formula

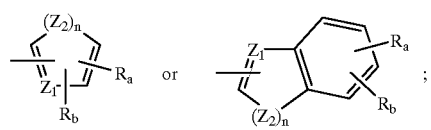

Z$_1$ is N, CR$_5$, (CH)$_m$—CR5 or (CH)$_m$—N, m being 1 or 2;

Z$_2$ is N, NR$_6$, O or S;

n is 0 or 1;

R$_1$, R$_2$, R$_3$, R$_4$, R$_5$ and R$_6$ are independently H, alkyl, aryl or heterocyclyl;

R$_7$ and R$_8$ are independently H, alkyl, aralkyl, carbamoyl, alkyl carbamoyl, dialkylcarbamoyl, acyl, alkoxycarbonyl, aralkoxycarbonyl, or aryloxycarbonyl, or R$_7$ and R$_8$ together may form

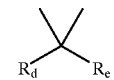

where R$_c$ is hydrogen or alkyl,

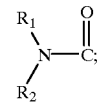

where R$_d$ and R$_e$ are independently hydrogen, or alkyl, or R$_d$ and R$_e$ together with the carbon atom to which they are attached may form a cycloalkyl group; and R$_a$ and R$_b$ are independently H, OH, alkyl, hydroxyalkyl, alkyl mercaptyl, thioalkyl, alkoxy, alkyoxyalkyl, amino, alkyl amino, carboxyl, acyl, halogen, carbamoyl, alkyl carbamoyl, aryl or heterocyclyl, where heterocyclyl is about a 4 to about a 10 membered ring structure in which one or more of the atoms in the ring is N, O or S, and which may be aromatic or non-aromatic.

15. The compound of claim 14 wherein P is selected from the group consisting of methanesulfonyl, trifluoromethanesulfonyl, benzenesulfonyl, p-toluenesulfonyl, p-methoxybenzenesulfonyl, phenacylsulfonyl, methoxycarbonyl, ethoxycarbonyl, 2,2,2-trichloroethoxycarbonyl, 2-trimethylsilylethyloxycarbonyl, tert-butoxycarbonyl, formyl, acetyl, benzoyl, trifluoroacetyl, benzyl and diphenylphosphinoyl.

16. The compound of claim 14 wherein P is selected from the group consisting of methanesulfonyl, trifluorobmethanesulfonyl, benzenesulfonyl, p-toluenesulfonyl, p-methoxybenzenesulfonyl and phenacylsulfonyl.

17. The compound of claim 16 wherein

Q is CH$_2$;

T is

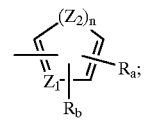

X is a straight or branched chain alkylene;

a=0;

Z is

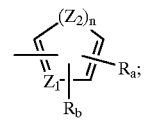

Z$_1$ is N, CR$_5$, (CH)$_m$—CR$_5$ or (CH)$_m$—N, m being 1 or 2;

$Z_2$ is N, $NR_6$, O or S, n being 0 or 1;

$R_1$, $R_2$, $R_5$ and $R_6$ are independently H or alkyl;

$R_7$ and $R_8$ are alkyl, or $R_7$ and $R_8$ together may form

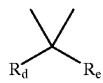

where $R_d$ and $R_e$ are independently hydrogen or alkyl, or together with the carbon atom to which they are attached may form a cycloalkyl group; and $R_a$ and $R_b$ are independently H, OH, alkyl, hydroxyalkyl, alkyl mercaptyl, thioalkyl, alkoxy, alkyoxyalkyl, amino, alkyl amino, carboxyl, acyl, halogen, carbamoyl, alkyl carbamoyl, aryl or heterocyclyl.

18. A compound of claim 14 selected from

[3aR-[3aα,4α,6a(R*),6aα]]-6-[4-[[1-[(3-chlorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide;

[3aR-[3aα,4α,6a(R*),6aα]]-6-[4-[[1-[(3-chlorothien-2-yl)methyl]propyl][4-methylbenzenesulfonyl]amino]-3-aminopyrid-2-ylamino]N-ethyl tetrahydro-2,2-dimethyl-4H-cyclopenta-1,3-dioxole-4-carboxamide; and

[3aR-[3aα,4α,6a(R*),6aα]]-6-[7-[[1-[(3-chlorothien-2-yl)methyl]propyl][4-methylbenzenesulfonyl]amino]-3H-imidazo[4,5-b]pyrid-3-yl]N-ethyl tetrahydro-2,2-dimethyl-4H-cyclopenta-1,3-dioxole-4-carboxamide.

* * * * *